United States Patent [19]
Leonardi et al.

[11] Patent Number: 6,071,920
[45] Date of Patent: Jun. 6, 2000

[54] 1-(N-PHENYLAMINOALKYL)PIPERAZINE DERIVATIVES SUBSTITUTED AT POSITION 2 OF THE PHENYL RING

[75] Inventors: Amedeo Leonardi, Milan; Gianni Motta, Barlassina; Carlo Riva, Varese; Rodolfo Testa, Vignate, all of Italy

[73] Assignee: Recordati S.A. Chemical and Pharmaceutical Company, Chiasso, Switzerland

[21] Appl. No.: 09/127,057

[22] Filed: Jul. 31, 1998

Related U.S. Application Data

[60] Provisional application No. 60/070,268, Dec. 31, 1997.

[30] Foreign Application Priority Data

Aug. 1, 1997 [IT] Italy ................................ MI97A1864

[51] Int. Cl.$^7$ ........................ A01N 43/60; A01N 31/495; C07D 403/00
[52] U.S. Cl. ............................ 514/255; 544/359
[58] Field of Search .............................. 514/255; 544/359

[56] References Cited

U.S. PATENT DOCUMENTS

| | | | |
|---|---|---|---|
| 3,472,854 | 10/1969 | Archer et al. ........................... | 260/268 |
| 3,635,976 | 1/1972 | Shetty ................................... | 260/256.4 |
| 4,017,624 | 4/1977 | Maruyama et al. ..................... | 424/250 |
| 4,060,526 | 11/1977 | Shetty ................................... | 260/268 |
| 4,085,107 | 4/1978 | Shetty ................................... | 260/256.4 |
| 4,205,173 | 5/1980 | Shetty ................................... | 546/218 |
| 5,008,267 | 4/1991 | Katakami et al. ...................... | 514/269 |
| 5,332,739 | 7/1994 | Katakami et al. ...................... | 514/252 |

FOREIGN PATENT DOCUMENTS

| | | |
|---|---|---|
| 0 598 123 | 5/1994 | European Pat. Off. . |
| 0 711 757 | 5/1996 | European Pat. Off. . |
| 2 405 441 | 8/1974 | Germany . |
| 2 263 110 | 7/1993 | United Kingdom . |
| WO 95/04049 | 2/1995 | WIPO . |
| WO 95/33743 | 12/1995 | WIPO . |

OTHER PUBLICATIONS

Anderson, K.E., Drugs, 35:447–494, (1988).
Bliss, C.I., Quart. J. Pharm. Pharmacolo. 11, 192–216, (1938).
Boong Kwon, H. et al., J. Org. Chem., 55:3114–3118, (1990).
Cheng, Y.C., et al., Biochem. Pharmacol., 22:, 3099–3108, (1973).
Craig A,.et al., J. Life Sci. 38, 117–127, (1985).
De Groat, W.C., Neurobiology of Incontinence, Ciba Foundation Symposium 151:27–56, (1990).
De Lean, A., et al., Am. J. Physiol., 235:E97–E102, (1978).
Diop L, et al., J. Neurochem., 41, 710–715, (1983).
Doleschall, G., et al., Tetrahedron, 32, 57–64, (1976).
Dray, A., J. Pharmacol. Methods, 13: 157–165, (1985).
Fargin, A., et al., Nature 335:358–360, (1988).
Francher D.E., et al., J. Med. Chem., 7:721–725, (1964).
Guarneri, L., et al., Drugs of Today, 30:91–98, (1994).
Guarneri, L., et al., Pharmocol. Res., 27:173–187, (1993).
Guarneri, L. et al., Pharmacol. Res., 24:175–187, (1991).
Lepor, H., Urology, 42:483–501, (1993).
Maggi, C.A. et al., Brain Res., 380:83–93, (1986).
Maggi, C.A. et al., J. Pharmacol. Exp. Ther., 230:500–513, (1984).
March, J., Advanced Org. Chem., 4th Ed., 1041–1042, (1992).
McGuire, M.A., et al., J. Org. Chem., 59:6683–6686, (1994).
McGuire, E.J., Campbell's Urology 5th Ed., 616–638, (1986).
Moser, R.C., Eur J. Pharmacol. 193:165–172, (1991).
Ramage, G.R., et al., J. Chem. Soc., 4406–4409, (1952).
Ruffman, J. Int. Med. Res., 16:317–330, (1988).
Sugasawa, T., et al., Chem. Pharm. Bull., 33:1826–1835, (1985).
S.N., Synlett, Note 12:328, (1996).
Tricklebank et al. Euro. J. Pharmacol., 117:15–24, (1985).
Wu, Y.H. et al., J. Med. Chem., 12:876–881, (1969).
Adachi et al., Chem. Pharm. Bulletin, 33: 1826–1835.

*Primary Examiner*—Mukund J. Shah
*Assistant Examiner*—Tamthom N. Truong
*Attorney, Agent, or Firm*—Darby & Darby

[57] ABSTRACT

Disclosed herein are novel compounds and methods for the treatment of disorders of the lower urinary tract. The novel compounds are aniline derivatives substituted at position 2 of the aniline ring. The methods comprise the administration of the novel compounds of the invention, and other compounds that bind to $5HT_{1A}$ receptors, for treating disorders of the lower urinary tract.

21 Claims, No Drawings

1-(N-PHENYLAMINOALKYL)PIPERAZINE DERIVATIVES SUBSTITUTED AT POSITION 2 OF THE PHENYL RING

This application claims priority under 35 U.S.C. § 119 from U.S. provisional patent application Ser. No. 60/070,268, filed Dec. 31, 1997, which is incorporated by reference herein in its entirety.

FIELD OF THE INVENTION

This invention relates to 1-(N-phenylaminoalkyl) piperazine derivatives substituted at position 2 of the phenyl ring, to pharmaceutical compositions containing them and to uses for such derivatives and compositions.

BACKGROUND OF THE INVENTION

In mammals, micturition (urination) is a complex process that requires the integrated actions of the bladder, its internal and external sphincters, the musculature of the pelvic floor, and neurological control over these muscles at three levels (in the bladder wall or sphincter itself, in the autonomic centers of the spinal cord, and in the central nervous system at the level of the pontine micturition center (PMC) in the brainstem (pons) under the control of cerebral cortex) (De Groat, *Neurobiology of Incontinence,* (Ciba Foundation Symposium 151: 27, 1990). Micturition results from contraction of the detrusor muscle, which consists of interlacing smooth muscle fibers under parasympathetic autonomic control from the sacral spinal cord. A simple voiding reflex is formed by sensory nerves for pain, temperature, and distension that run from the bladder to the sacral cord. However, sensory tracts from the bladder also reach the PMC, resulting in the generation of nerve impulses that normally suppress the sacral spinal reflex arc controlling bladder emptying. Thus, normal micturition is initiated by voluntary suppression of cortical inhibition of the reflex arc and by relaxation of the muscles of the pelvic floor and the external sphincter. Finally, the detrusor muscle contracts and voiding occurs.

Abnormalities of lower urinary tract function, e.g., dysuria, incontinence, and enuresis, are common in the general population. Dysuria includes urinary frequency, nocturia, and urgency, and may be caused by cystitis, prostatitis or benign prostatic hypertrophy (BPH) (which affects about 70% of elderly males), or by neurological disorders. Incontinence syndromes include stress incontinence, urgency incontinence, and overflow incontinence. Enuresis refers to the involuntary passage of urine at night or during sleep.

Prior to the work of the present inventors, treatment of neuromuscular dysfunction of the lower urinary tract has involved administration of compounds that act directly on the bladder muscles, such as flavoxate, a spasmolytic drug (Ruffman, *J. Int. Med. Res.* 16:317, 1988) also active on the PMC (Guarneri et al., *Drugs of Today* 30:91, 1994), or anticholinergic compounds such as oxybutynin (Andersson, *Drugs* 35:477, 1988). The use of $\alpha_1$-adrenergic receptor antagonists for the treatment of BPH is also common but is based on a different mechanism of action. (Lepor, *Urology,* 42:483, 1993).

However, treatments that involve direct inhibition of the pelvic musculature (including the detrusor muscle) may have unwanted side effects such as incomplete voiding or accommodation paralysis, tachycardia and dry mouth (Andersson, *Drugs* 35:477, 1988). Thus, it would be advantageous if compounds were available that act via the peripheral or central nervous system to, for example, affect the sacral spinal reflex arc and/or the PMC inhibition pathways in a manner that restores normal functioning of the micturition mechanism.

1-(N-phenyl-N-cyclohexylcarbonyl-2-aminoethyl)-4-(2-methoxyphenyl)piperazine (compound A)

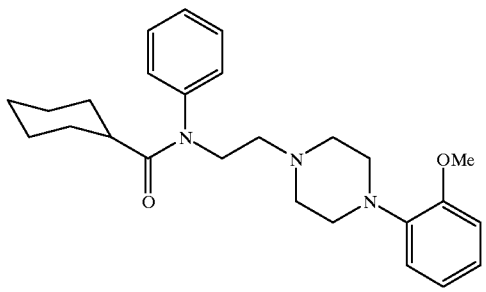

(A)

is described in GB 2 263110 A and is reported to be a 5-HT$_{1A}$ receptor antagonist. It is also disclosed that it can be used for the treatment of central nervous system disorders, for example as an anxiolytic agent in the treatment of anxiety.

The compounds of the present invention, described below, are structurally different from compound A because of the novel substituents present on the aniline ring at the 2 position. Other differences between the compounds of the present invention and those disclosed in GB 2 263110 A are the substitutions on the aromatic ring at position 4 of the piperazine ring. These structural variations are neither disclosed nor suggested by GB 2 263110 A, particularly with regard to compounds that can be used to improve urinary tract function.

These structural variations result in compounds that are more potent than compound A in pharmacological tests predictive of activity on the lower urinary tract, in particular for activity against urinary incontinence.

Other compounds which have been found by the present inventors to be useful in the methods of the present invention, e.g., treatment of disorders of the urinary tract, are disclosed in U.S. Pat. No. 4,205,173; EP 711,757; U.S. Pat. Des. No. 2,405,441; *Chem. Pharm. Bull.* 33:1823–1835 (1985), and *J. Med. Chem.* 7:721–725 (1964), all of which are incorporated by reference.

SUMMARY OF THE INVENTION

In one aspect the invention is directed to compounds of formula I:

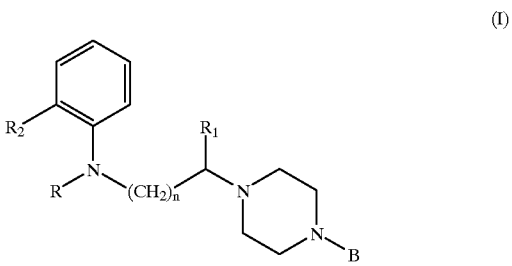

(I)

wherein
R is a hydrogen atom, an alkylcarbonyl, a cycloalkylcarbonyl, a substituted cycloalkylcarbonyl or a monocyclic heteroarylcarbonyl group, $R_1$ is a hydrogen atom or a lower alkyl group, $R_2$ is an alkoxy, phenoxy, nitro, cyano, acyl, amino, acylamino, alkylsulphonylamino, alkoxycarbonyl, aminocarbonyl, N-alkylaminocarbonyl, N,N-dialkylaminocarbonyl, N-acylaminocarbonyl, halo, trifluoromethyl or polyfluoroalkoxy group, B is a mono or bicyclic aryl, a mono or bicyclic heteroaryl or benzyl group, all optionally substituted, and n is 1 or 2.

In another aspect, the invention is directed to compounds of formula I A:

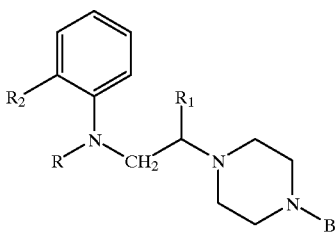

(1A)

wherein

R is a hydrogen atom, an alkylcarbonyl, a cycloalkylcarbonyl or a monocyclic heteroarylcarbonyl group, $R_1$ is a hydrogen atom or a lower alkyl group, $R_2$ is an alkoxy, phenoxy, nitro, cyano, acyl, amino, acylamino, alkylsulphonylamino, alkoxycarbonyl, aminocarbonyl, N-alkylaminocarbonyl, N,N-dialkylaminocarbonyl, N-acylaminocarbonyl, halo, trifluoromethyl or polyfluoroalkoxy group, B is a substituted monocyclic aryl group, an optionally substituted bicyclic aryl group, an optionally substituted mono or bicyclic heteroaryl group, or a substituted benzyl group, with the provisos that:

if both R and $R_1$ are hydrogen and $R_2$ is a nitro group, then B cannot be a phenyl, 2-methoxyphenyl, 4-chlorophenyl, 3-acetylphenyl, 3,4,5-trimethyoxyphenyl, 2-chloro-4-methylphenyl, or 2-pyridyl group; and if B is aryl and is substituted by an alkoxy group, then the alkoxy group must be at position 2.

In yet another aspect, the invention is directed to compounds of formula I B:

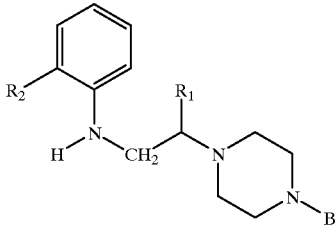

(1B)

wherein $R_1$ is a hydrogen atom or a lower alkyl group, $R_2$ is an alkoxy, phenoxy, nitro, cyano, acyl, alkoxycarbonyl, acylamino, alkylsulphonylamino, aminocarbonyl, N-alkylaminocarbonyl, N,N-dialkylaminocarbonyl, N-acylaminocarbonyl, halo, trifluoromethyl or polyfluoroalkoxy group, B is a substituted monocyclic aryl group, an optionally substituted bicyclic aryl group, an optionally substi-tuted mono or bicyclic heteroaryl group, or a substituted benzyl group with the provisos that:

if $R_1$ is hydrogen and $R_2$ is a nitro group then B cannot be a phenyl, 2-methoxyphenyl, 4-chlorophenyl, 3-acetylphenyl, 3,4,5-trimethoxyphenyl, 2-chloro-4-methylphenyl, or 2-pyridyl group; and if B is aryl and is substituted by an alkoxy group, then the alkoxy group must be at position 2.

The invention also includes the enantiomers, diastereomers, N-oxides, crystalline forms, hydrates and pharmaceutically acceptable salts of these compounds, as well as metabolites of these compounds having the same type of activity (hereafter sometimes referred to as "active metabolites").

As used herein with reference to variable R, alkylcarbonyl radicals include $C_1$–$C_6$ alkylcarbonyl, cycloalkylcarbonyl includes cyclohexylcarbonyl, substituted cycloalkylcarbonyl includes cyclohexylcarbony substituted with alkyl or aryl groups and monocyclic heteroaryl radicals include monocyclic aromatic radicals of 5 to 7 ring atoms containing one or more hetero atoms (e.g., oxygen, nitrogen, and sulfur). Monocyclic heteroarylcarbonyl has the same definition as monocyclic heteroaryl, but also comprises a carbonyl group linked to a carbon atom of the ring.

As used herein with reference to variable B, a mono or bicyclic aryl radical means an aromatic radical having 6 to 12 carbon atoms (e.g., phenyl or naphthyl) which is substituted by one or more substitutents.

Preferred substitutents for aryl radicals are lower alkyl, lower alkoxy (e.g., methoxy, ethoxy, propoxy, and butoxy), lower haloalkoxy (e.g., 2,2,2-trifluoroethoxy) halogen, amino, acylamino, alkylsulfonylamino, and (lower) alkylamino substituents.

As used with respect to variable B, monocyclic heteroaryl radical has the same meaning as for R, above, and bicyclic heteroaryl radical means a bicyclic aromatic radical containing one or more heteroatoms (e.g., nitrogen, oxygen, sulfur) and 9 to 12 ring atoms.

Benzyl radicals, with respect to variable B, include phenylmethyl radicals which may be optionally substituted by one or more substituents. Preferred substituents for the benzyl radicals are alkyl, alkoxy, halogen, nitro, cyano, amido, amino, alkylamino, acylamino, alkylsulphonylamino or acyl substituents. Preferred substituents at B are optionally substituted monocyclic aryl and bicyclic heteroaryl. Most preferred substituents at B are alkoxyphenyl and mononitrogen-containing bicyclic heteroaryl.

Preferred substituents are $R_1$ are hydrogen and methyl.

Preferred substituents at $R_2$ are nitro, cyano, acyl, and aminocarbonyl. Most preferred at $R_2$ is nitro. A preferred value for n is 1.

The invention further provides pharmaceutical compositions comprising a compound of formula I or an enantiomer, diastereomer, N-oxide, crystalline form, hydrate or pharmaceutically acceptable salt of the compound, in admixture with a pharmaceutically acceptable diluent or carrier.

In another aspect, the present invention is directed to methods for reducing the frequency of bladder contractions due to bladder distension by administering one or more selected compounds of Formula I to a mammal (including a human) in need of such treatment, in an amount or amounts effective for the particular use.

In a further aspect, the present invention is directed to methods for treating disorders of the urinary tract in a subject in need of such treatment, comprising administering an effective amount of a compound of Formula 1 to ameliorate at least one of urinary urgency, increased urinary frequency, incontinence, urine leakage, enuresis, dysuria, urinary hesitancy, and difficulty in emptying bladder.

In yet another aspect, the invention is directed to methods for blocking 5-HT$_{1A}$ serotonergic receptors, and, by virtue of this inhibitory activity, to methods for the treatment of CNS disorders due to serotonergic dysfunction such as anxiety, depression, hypertension, sleep/wake cycle disorders, feeding behavior, sexual function and cognition disorders in mammals, particularly in humans, by delivering to the environment of the 5-HT$_{1A}$ serotonergic receptors, e.g., to the extracellular medium (or by administering to a mammal possessing such receptors) an effective amount of a compound of the invention.

DETAILED DESCRIPTION OF THE INVENTION

All patents, patent applications, and literature references cited in the specification are hereby incorporated by reference in their entirety. In the case of inconsistencies, the present disclosure, including definitions, will prevail.

The activity of the compounds of the invention as inhibitors of frequency of micturition renders them useful for the treatment of neuromuscular dysfunctions of the lower urinary tract in mammals, including without limitation dysuria, incontinence and enuresis.

Surprisingly, the introduction of selected substituents at position 2 of the aniline ring in compounds of Formula I confers upon these compounds a distinctly higher potency with regard to compound A and also to the isomers bearing the same substituent at position 3 or 4. This information was obtained by testing compound A and the corresponding 2, 3 and 4 nitroaniline derivatives (Example 2 and compounds B and C) in a rat model. The rhythmic contraction of rat bladders was induced by filling the bladders with a physiologic solution. The effect of test compounds of the invention on the frequency and amplitude of the contractions was evaluated. Of particular interest is the time of disappearance of induced contractions. (ED$_{10\ min}$ in Table 1, Example 46 below).

The same behavior (greater potency for 2-substituted derivatives) was also discovered for compounds of the invention where R is a hydrogen atom. Data in Table 1 (in particular, ED$_{50}$ (frequency)) show that the 2-substituted compounds of the invention are clearly more potent inhibitors of the frequency of urinary bladder contractions.

The effect of the drugs currently available for administration to humans for treatment of neuromuscular function of the lower urinary tract (flavoxate and oxybutynin) on the above-described rat model is also shown, for comparative purposes, in Table 1.

The compounds of the invention are more potent and acted for a longer period of time (as measured by duration of bladder quiescence with no contractions) than did compounds A, flavoxate, and oxybutynin. Moreover, in contrast to oxybutynin, the compounds of the invention did not affect the amplitude of the contractions (no effect on ED$_{50}$ (amplitude) in Table 1), suggesting no impairment of bladder contractility that could result in residual urine being left in the bladder after micturition.

In addition, the beneficial effect on the lower urinary tract of the compounds of the invention has been shown in a cystometry model in conscious rats, where the compounds of the invention are also superior to compd A and the reference drugs. In fact, compounds of the invention increased the bladder capacity at doses lower than compound A and flavoxate (oxybutynin does not affect bladder capacity) (Table 2). Furthermore, in contrast to the effects of oxybutynin, no impairment of bladder contractility (decrease in MP) was observed.

Finally, the compounds of the invention have a high and selective affinity for the 5-HT$_{1A}$ receptor, an affinity and selectivity displayed to a much lesser extent by compound A, (Table 3). The compounds of the invention have also been shown to antagonize both pre- and post-synaptic 5-HT$_{1A}$ receptors much more potently than compound A (Table 4), strongly suggesting a role for the 5-HT$_{1A}$ receptor in the action of the compounds of the invention.

Subjects who can benefit from administration of the compounds and compositions of the invention include humans who are affected by neuromuscular dysfunction of the lower urinary tract, described by E. J. McGuire in "Campbell's UROLOGY" 5$^{th}$ Ed. 616–638, 1986, W. B. Saunders Company, and also include patients affected by any physiological dysfunction related to impairment of 5-HT$_{1A}$ receptor function. Such dysfunctions include, without limitation, central nervous system disorders such as depression, anxiety, eating disorders, sexual dysfunction, addiction, and related problems.

The present invention encompasses pharmaceutical formulations comprising the compounds disclosed above, as well as methods employing these formulations for treating neuromuscular dysfunction of the lower urinary tract such as dysuria, incontinence, enuresis, and the like. Dysuria includes urinary frequency, nocturia, urgency, and difficulty in emptying the bladder, i.e., a suboptimal volume of urine is expelled during micturition.

Incontinence syndromes include stress incontinence, urgency incontinence, and overflow incontinence. Enuresis refers to the involuntary passage of urine at night or during sleep.

Without wishing to be bound by theory, it is believed that administration of the 5-HT$_{1A}$ receptor antagonists of the invention prevents unwanted activity of the sacral reflex arc and/or cortical mechanisms that control micturition. Thus it is contemplated that a wide range of neuromuscular dysfunctions of the lower urinary tract can be treated using the compounds of the present invention.

An "effective amount" of the compound for treating a urinary disorder is an amount that results in measurable amelioration of at least one symptom or parameter of the disorders described above.

An effective amount for treating the disorder can easily be determined by empirical methods known to those of ordinary skill in the art, such as by establishing a matrix of dosages and frequencies of administration and comparing a group of experimental units or subjects to each point in the matrix. The exact amount to be administered to a patient will vary depending on the state and severity of the disorder and the physical condition of the patient. A measurable amelioration of any symptom or parameter can be determined by a physician skilled in the art or reported by the patient to the physician. It will be understood that any clinically or statistically significant attenuation or amelioration of any symptom or parameter of urinary tract disorders is within the scope of the invention. Clinically significant attenuation or amelioration means perceptible to the patient and/or to the physician.

For example, a single patient may suffer from several symptoms of dysuria simultaneously, such as, for example, urgency and excessive frequency of urination, either or both of which may be reduced using the methods of the present invention. In the case of incontinence, any reduction in the frequency or volume of unwanted passage of urine is considered a beneficial effect of the present methods of treatment.

The compounds of the present invention may be formulated into liquid dosage forms with a physiologically acceptable carrier, such as, for example, phosphate buffered saline or deionized water. The pharmaceutical formulation may also contain excipients, including preservatives and stabilizers, that are well-known in the art. The compounds can be formulated into solid oral or non-oral dosage units such as, for example, tablets, capsules, powders, and suppositories, and may additionally include excipients, including without limitation lubricant(s), plasticizer(s), colorant(s), absorption enhancer(s), bactericide(s), and the like.

Modes of administration include oral and enteral, intravenous, intramuscular, subcutaneous, transdermal, transmucosal (including rectal and buccal), and by-inhalation routes. Preferably, an oral or transdermal route is used (i.e., via solid or liquid oral formulations, or skin patches, respectively).

The amount of the agent to be administered can range from between about 0.01 and about 25 mg/kg/day, preferably from between about 0.1 and about 10 mg/kg/day and most preferably from betweem about 0.2 and about 5 mg/kg/day. It will be understood that the single pharmaceutical formulations of the present invention need not contain the entire amount of the agent that is effective in treating the disorder, as such effective amounts can be reached by administration of a plurality of doses of such pharmaceutical formulations.

In a preferred embodiment of the present invention, compounds are formulated in capsules or tablets, each preferably containing 50–200 mg of the compounds of the invention, and are most preferably administered to a patient at a total daily dose of 50–400 mg, preferably 150–250 mg, and most preferably about 200 mg for relief of urinary incontinence and dysfunctions amenable to treatment with 5-HT$_{1A}$ receptor ligands.

The methods, tables and examples provided below are intended to more fully describe preferred embodiments of the invention and to demonstrate its advantages and applicability, without in any way limiting the scope of the invention.

SYNTHESIS OF THE COMPOUNDS OF THE INVENTION

The compounds of the invention may be prepared by the methods illustrated in the following reaction schemes, or by modifications thereof, using readily available starting materials, reagents and conventional synthesis procedures well known to those of ordinary skill in the art.

Unless otherwise specified, the substituents of the compounds and intermediates present in the reaction schemes are defined in the same manner as they are defined above in formula I. One method to synthesize compounds of formula I is depicted in Scheme 1.

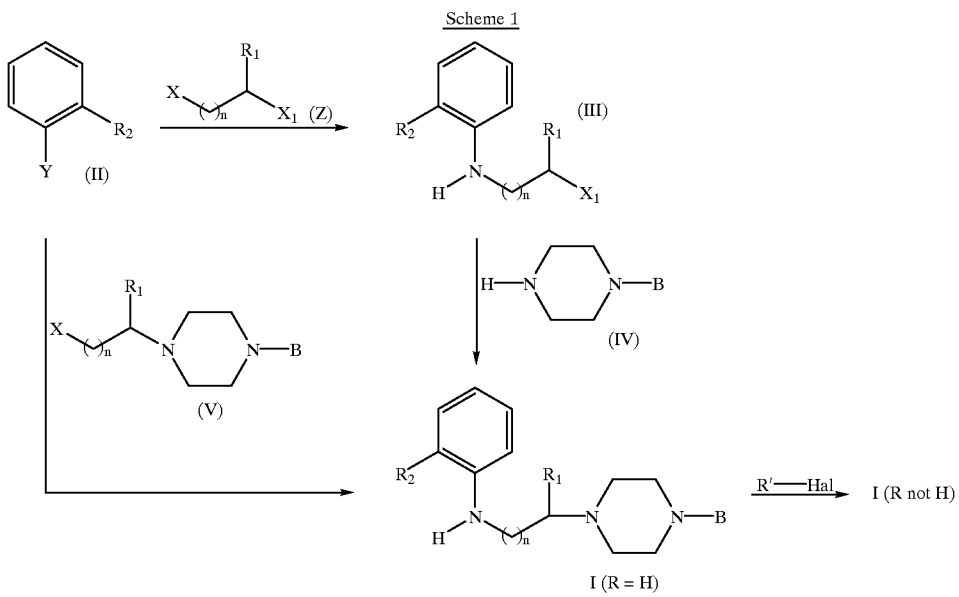

Ortho-substituted anilines of formula II (Y=NH$_2$) are alkylated with 1,ω-disubstituted alkanes (Z) to give product III. The reaction is carried out in an inert organic solvent, preferentially a polar aprotic solvent such as N,N-dimethylformamide (DMF), dimethylsulfoxide (DMSO), dioxane, tetrahydrofuran (THF), acetone, acetonitrile or chlorinated solvents such as dichloromethane, chloroform, 1,2-dichloroethane or a protic solvent such as N-butanol (n-BuOH). The reactions are generally performed at a temperature between 0° C. and +120° C., in the presence of a proton acceptor such as triethylamine (Et$_3$N), diisopropylethylamine, or the like, and optionally in the presence of potassium iodide.

In compounds of formula Z, X and X$_1$ can be Cl, Br, I, aryl, or alkylsulfonyloxy groups.

Intermediates of formula III are used in the alkylation of suitable piperazine derivatives IV to give the compounds of formula I (where R=H).

These alkylations may be carried out in a chlorinated solvent such as dichlorometane, chloroform or 1,2-dichloroethane, or in a polar aprotic solvent such as DMF, THF, acetone, acetonitrile, or in a polar protic solvent such as n-BuOH, etc., or in an apolar solvent such as toluene, benzene, n-heptane, etc., at a temperature between 0° C., and 120° C., optionally in the presence of a proton acceptor, such as $Et_3N$, 4-dimethylaminopyridine, potassium carbonate, cesium carbonate, and the like, and optionally in the presence of potassium iodide.

Piperazines of formula IV which are not commercially available may be prepared by reaction of the suitable B—$NH_2$ derivatives (which generally may be easily obtained by reduction of the corresponding B—$NO_2$ derivatives) with bis-(2-chloroethyl)amine or bis-(2-hydroxyethyl)amine in presence of excess hydrogen chloride. These reactions can be performed in aprotic solvents such as dimethylformamide, diglyme or toluene at a temperature between +40° C. and the reflux temperature of the solvent, generally in the presence of a base such as potassium carbonate, cesium carbonate, or the like, and optionally in the presence of potassium iodide.

Compounds of formula V can be conveniently prepared starting from compounds V in which X is a COO-lower alkyl group and n is n−1. Conventional reduction procedures (e.g., use of lithium aluminum hydride or other metal complex hydrides) afford the corresponding compounds V in which X is $CH_2OH$ and n is n−1, which can be in turn conventionally converted into compounds of formula V in which X is a leaving group as described above. The starting esters can be prepared by well known Michael reactions or by the nucleophilic displacement reaction of a monosubstituted piperazine on the appropriate 2,3-unsaturated ester or 2-haloester.

Alternative procedures to obtain compounds of formula V consists in alkylating the appropriate monosubstituted piperazine derivatives with a compound with the formula X—$CH(R_1)(CH_2)_{n-1}CH_2$—OPrG or X—$(CH_2)_nCH(R_1)$—X where X is a leaving group and n has the same meaning as above, and PrG is a protecting group (e.g. O-tetrahydropyranyl), which can be removed after alkylation of the piperazine.

Another approach to synthesize intermediate compounds of formula III utilizes starting materials with structure II (Y=halogen). These starting materials are reacted with compounds of formula Z in which X and $X_1$ are, respectively, $NH_2$ and OH. These alkylation reactions are carried out in an aprotic solvent such as DMF, toluene, or in a polar protic solvent such as n-BuOH, etc., at a temperature between +40° C. and +140° C., in general using one equivalent or excess of a reagent of formula Z (X=$NH_2$) as a proton acceptor, as described by G. Doleschall et al., Tetrahedron, 32, 57–64 (1976). The resulting aminoalcohols of formula III ($X_1$=OH) are reacted with a chlorinating agent such as $POCl_3$, $SOCl_2$ or $PCl_5$ to give the intermediates, also of formula III ($X_1$=Cl), or with an alkyl or arylsulfonyl chloride to give the corresponding sulfonyl esters. These reactions are carried out in an aprotic solvent such as chloroform, DMF, pyridine, and the like at a temperature between +50° C. and the reflux temperature of the solvent.

Compounds of formula I (R=H) may also be obtained by alkylation of compounds of formula II (Y=$NH_2$) with intermediates of formula V, in which B, $R_1$ and n have the same meanings as above and X is a halogen atom such as chlorine or bromine, or a leaving group such as methanesulfonyloxy or p-toluenesulfonyloxy groups.

These reactions may be carried out without solvent or in an aprotic solvent such as dichloromethane, chloroform, DMF, THF, acetone, acetonitrile or in a protic solvent such as n-butanol, etc. at a temperature between 0° C. and +160° C., optionally in the presence of a proton acceptor, such as $Et_3N$, potassium carbonate, cesium carbonate, 4-dimethylaminopyridine and the like, and optionally in the presence of potassium iodide.

Compounds of formula I where $R_2$ is CN can be also obtained from the compounds of formula I in which $R_2$ is $CONH_2$ by dehydration reactions. $P_2O_5$, $PCl_5$, $Ph_3P$, and the like may be used as dehydrating agents (J. March, Advanced Organic Chemistry, IV Ed., page 1041, Wiley Interscience, 1992). Dehydration reactions may be carried out in a chlorinated solvent such as dichloromethane, chloroform, carbon tetrachloride or in an aprotic solvent such as DMF, toluene, etc. at a temperature between +40° C. and the reflux temperature of the solvent, optionally in the presence of a base such as $Et_3N$.

Alternatively, compounds of formula I (R=H) may be obtained by arylation of intermediates of formula V (X=$NH_2$) with a starting material of formula II (Y=Cl, Br, F, I or trifluoromethanesulphonyloxy). These reactions may be carried out using the same solvents and conditions as described above or by employing palladium complex catalysis (Synlett, p. 329 (1996)).

Compounds of formula I in which $R_2$ is COalk can be synthesized from compounds I in which $R_2$ is H by an acylation reaction that can be carried out using boron trichloride as a Lewis acid and acetonitrile as a reagent in an aprotic solvent such as chloroform, 1,2-dichloroethane, toluene, etc. at temperatures between 0° C. and 100° C., followed by acidic hydrolysis by treatment with HCl at 100° C., (T. Sugasawa et al., Chem. Pharm. Bull., 33, 1826–1835 (1985)).

Compounds of formula I (R=H) are acylated to give compound I (R other than H) by reaction with an appropriate acyl halide R'Hal in which R' represents an alkylcarbonyl, cycloalkylcarbonyl or monocyclic heteroarylcarbonyl group and Hal represents a halogen atom. The reaction can be performed in aprotic solvents such as dichloromethane, chloroform, 1,2-dichloroethane, DMF, acetone, acetonitrile, toluene, etc., at temperatures between 0° C. and 100° C., optionally in the presence of an organic base as a proton acceptor such as $Et_3N$, diisopropylethylamine (DIPEA), 4-dimethylaminopyridine, and the like.

Alternatively, compounds with formula I (i.e., where $R_2$=Br, I, $OSO_2F$ or $OSO_2CF_3$) in which R is as defined above, but is not hydrogen, may be used to synthesize compounds of formula I in which $R_2$ is CN, $CONH_2$, $COCH_3$ or $COOCH_3$ by reaction of reagents such as trimethylsilyl isocyanate and t-butyl lithium (J. Org. Chem. 55, 3114 (1990)), lithium cyanide and tetrakis (triphenylphosphine)palladium(0) (EP711757), carbon monoxide-methanol and palladium diacetate in the presence of 1,3-diphenylphosphinopropane (J. Org. Chem. 59, 6683 (1994)). Such reactions may be carried out in polar or apolar solvent such as THF, toluene, benzene, DMSO, and the like.

Another method to synthesize compounds of formula I in which $R_1$ is H is depicted in Scheme 2, below.

Scheme 2

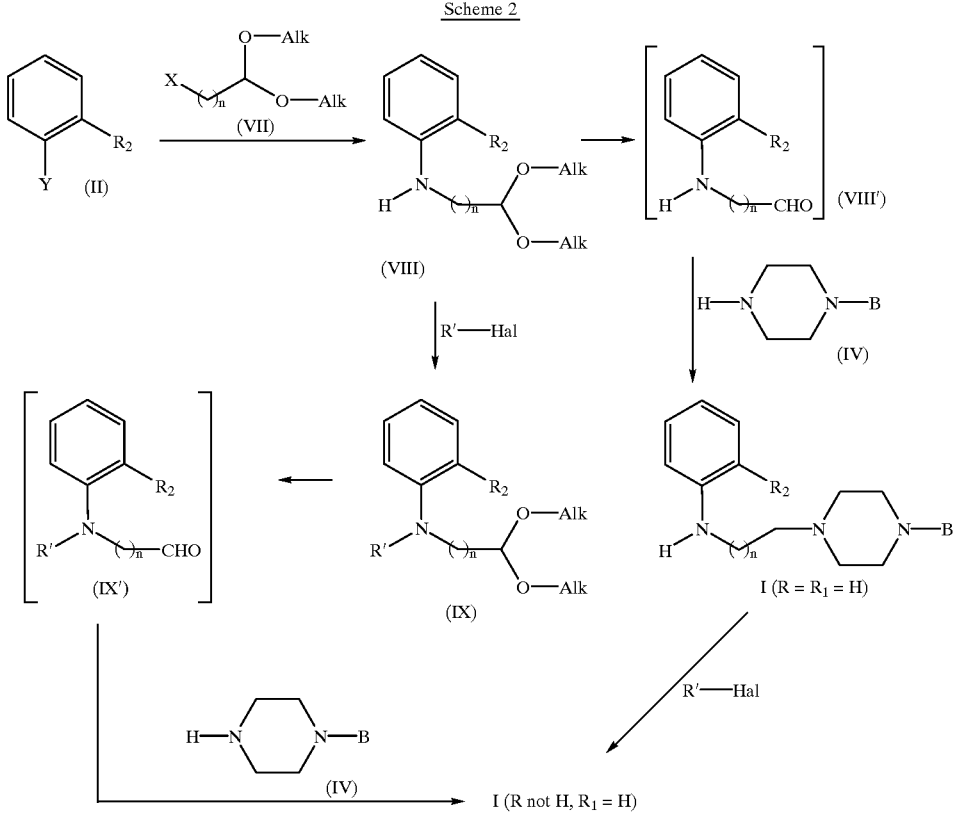

Ortho-substituted halobenzenes of formula II (Y=halo) are used to arylate protected aminoalkylaldehydes of formula VII (X=NH$_2$) to give the corresponding protected arylaminoalkylaldehydes VIII. The reaction may be carried out in an aprotic solvent such as pyridine, DMF, toluene, or the like at a temperature between +40° C. and 120° C., optionally in the presence of a base such as Et$_3$N or employing palladium complex catalysts as above.

Another route for the preparation of intermediates of formula VIII consists in alkylating compounds of formula II (Y=NH$_2$) with protected reactive compounds of formula VII (X=halo) by conventional procedures known to those skilled in the art. Compounds with formula VIII are stable and are deprotected by standard methods just before their use in the following steps.

Aldehydes of formula VIII', obtained from deprotection of compounds with formula VIII, may be reacted without isolation with N-substituted piperazines IV under reductive conditions to give compounds of formula I (R=R'=H). These reactions may be carried out in polar solvents such as methanol, ethanol or in chlorinated solvents, such as dichloromethane, chloroform, and the like, using alkali borohydrides such as NaBH$_4$ and NaBH$_3$CN, NaBH(OAc)$_3$ or using borane complexes such as BH$_3$—Py, optionally in the presence of acidic promoter, such as acetic acid, at temperatures between +10° C. and 100°C.

Compounds of formula I (R=R'=H) may be acylated with R'Hal to give compounds of formula I where R is an alkylcarbonyl group by carrying out the reactions in the same conditions as described above for the final step of Scheme 1. Alternatively, intermediates of formula VIII may be acylated with R'Hal to give compounds of formula IX using the same conditions as described above.

Intermediates of formula IX are deprotected by well-known methods just before their use in the final step to give the corresponding aldehydes (IX'), which may be reacted with appropriate N-substituted piperazines of formula IV using alkali borohydrides such as NaBH$_4$, NaBH$_3$CN or NaBH(OA)$_3$, optionally in the presence of catalytic amounts of acetic acid, or of a titanium catalyst such as titanium tetraisopropoxide, yielding compounds of formula I. These reactions may be carried out in chlorinated solvents such as dichloromethane or chloroform, or in polar aprotic solvents such as methanol or ethanol at temperatures between +10° C. and +100° C.

Compound AA
1-(N-phenyl-2-aminoethyl)-4-(2-methoxyphenyl)piperazine

Compounds B and D
1-[N-(3-nitrophenyl)-N-cyclohexylcarbonyl-2-aminoethyl]-4-(2-methoxyphenyl)piperazine (Compound B) and 1-[N-(3-nitrophenyl)-2-aminoethyl]-4-(2-methoxyphenyl) piperazine (Compound D)

Compounds C and E
1-[N-(4-nitrophenyl)-N-cyclohexylcarbonyl-2-aminoethyl]-4-(2-methoxyphenyl)piperazine (Compound C) and 1-[N-(4-nitrophenyl)-2-aminoethyl]-4-(2-methoxyphenyl) piperazine (Compound E)

EXAMPLE 1

1-[N-(2-nitrophenyl)-2-aminoethyl]-4-(2-methoxyphenyl)piperazine

A mixture of 3.03 g of 2-chloronitrobenzene, 4.52 g of 1-(2-aminoethyl)-4-(2-methoxyphenyl)piperazine, and 3.18 g of anhydrous potassium carbonate in 30 mL of n-butanol was stirred for 32 h at reflux. After cooling, the mixture was poured into H₂O, then extracted with EtOAc and the organic phase dried on Na₂SO₄. The crude obtained by evaporating the solvent was purified by flash chromatography (EtOAc-petrolium ether 4:6) and the residue obtained after evaporation of the solvents was taken up with Et₂O, stirred and filtered giving 2.2 g (31%) of the title compound. Melting point: 117–118° C.

¹H-NMR (CDCl₃, δ): 8.50 (bs, 1H, NH), 8.19 (d, 1H, aniline H3), 7.45 (dd, 1H, aniline H5), 7.08–6.78 (m, 5H, aniline H6 and methoxyphenyl ring CHs), 6.63 (dd, 1H, aniline H4), 3.86 (s, 3H, OCH₃), 3.40 (dt, 2H, NHC$\underline{H}$₂CH₂), 3.27–3.04 (m, 4H, piperazine protons), 2.80–2.62 (m, 6H, NHCH₂C$\underline{H}$₂ and piperazine protons).

EXAMPLE 2

1-[N-(2-nitrophenyl)-N-cyclohexylcarbonyl-2-aminoethyl]-4-(2-methoxyphenyl) piperazine Cyclohexanecarbonyl chloride (0.98 mL) and triethylamine (1.03 mL) were added in sequence to a solution containing 2.1 g of the compound described in example 1 and 15 mL of 1,2-dichloroethane. The mixture was stirred for 16 h at reflux. Finally it was cooled, diluted with CHCl₃, washed with NaOH 1 N and H₂O. The organic phase was dried on anhydrous Na₂SO₄ and the crude obtained after evaporation of the solvents was purified via flash chromatography (EtOAc-petrolium ether 1:1) and subsequently crystallized from cyclohexane giving 1.79 g (65%) of the title compound. Melting point: 119–121° C.

¹H-NMR (CDCl₃, δ): 8.04 (d, 1H, nitrophenyl ring H3), 7.65–7.47 (m, 3H, nitrophenyl ring H4,5,6), 7.10–6.75 (m, 4H, methoxyphenyl ring CHs), 4.15–3.92 (m, 1H, C(O)NC($\underline{H}$)CH₂), 3.83 (s, 3H, OCH₃), 3.70–3.50 (m, 1H, C(O)NC$\underline{H}$(H)CH₂), 3.10–2.80 (m, 4H, piperazine protons), 2.80–2.40 (m, 6H, piperazine protons and C(O)NCH₂C$\underline{H}$₂), 2.10–0.75 (m, 11H, cyclohexyl protons).

By conventional methods, the following salts of compound of Example 2 were prepared:
monohydrochloride, m.p. 183–187° C. (Me₂CO—Et₂O);
monomethanesulphonate, m.p. 150–153° C. (Me₂CO);
monomethanesulphonate hydrate, m.p. 136–140° C.

EXAMPLE 3

1-[N-(2-trifluoromethoxyphenyl)-2-aminoethyl]-4-(2-methoxyphenyl)piperazine

A solution of 2.09 g of 2-trifluoromethoxyaniline and 3.15 g of 1-(2-chloroethyl)-4-(2-methoxyphenyl)piperazine in 20 mL of n-butanol was stirred at 100° C. for 2 hrs. The mixture was then cooled, diluted with H₂O, alkalinized with 2 N NaOH and extracted with CHCl₃. The organic phase was dried on anhydrous Na₂SO₄, evaporated until dry and the crude purified via flash chromatography (EtOAc-petrolium ether 3:7) and subsequently crystallized from EtOH giving 0.55 g (12%) of the title compound. Melting point: 69.5–71° C.

¹H-NMR (CDCl₃, δ): 8.02–7.85 (br, 1H, NH), 7.43–7.27 (m, 2H, aniline CHs), 7.03–6.80 (m, 4H, methoxyphenyl ring CHs), 6.72 (dd, 1H, aniline CH), 6.57 (t, 1H, aniline CH), 3.86 (s, 3H, OCH₃), 3.43–3.23 (m, 2H, NHC$\underline{H}$₂CH₂), 3.23–3.03 (m, 4H, piperazine protons), 2.85–2.60 (m, 6H, piperazine protons and NHCH₂C$\underline{H}$₂).

EXAMPLE 4

1-[N-(2-trifluoromethoxyphenyl)-N-cyclohexylcarbonyl-2-aminoethyl]-4-(2-methoxyphenyl)piperazine The title compound was prepared following the procedure described for the compound in example 2, except that the compound in example 3 was used in place of the compound in example 1 (i.e. 4-dimethylaminopyridine replaced triethylamine) and heated for 1.5 h at reflux. The raw material was purified via flash chromatography (EtOAc-petrolium ether 4:6). Yield: 44%.

¹H-NMR (CDCl₃, δ): 7.48–7.25 (m, 4H, trifluoromethoxyaniline ring CHs), 7.02–6.81 (m, 4H, methoxyphenyl ring CHs), 4.40–4.20 (m, 1H, C(O)NCH$\underline{H}$CH₂), 3.84 (s, 3H, OCH₃), 3.36–3.18 (m, 1H, C(O)NC$\underline{H}$HCH₂), 3.10–2.90 (m, 4H, piperazine protons), 2.75–2.45 (m, 6H, piperazine protons and C(O)NCH₂C$\underline{H}$₂), and 2.03–1.80 (m, 1H, CHC(O)), 1.75–0.80 (m, 10H, cyclohexyl protons).

EXAMPLE 5

1-[N-(2-phenoxyphenyl)-2-aminoethyl]-4-(2-methoxyphenyl) piperazine.3HCl

The title compound was prepared following the procedure described for the compound in example 3, except that 2-phenoxyaniline was used in place of 2-trifluoromethoxyaniline. The raw material was purified via flash chromatography (EtOAc). The residue was dissolved in ethanol, the solution was acidified by using 2 N HCl in ethanol and subsequently Et₂O was added giving 45% of the title compound after filtration. Melting point: 184–187° C.

¹H-NMR (DMSO-d₆, δ): 8.70–7.60 (m, 4H, 3⁺NH and NH), 7.32 (t, 2H, aromatics), 7.10–6.85 (m, 9H, aromatics), 6.80 (dd, 1H, aromatic), 6.63 (t, 1H, aromatic), 3.78 (s, 3H, OCH₃), 3.65–3.00 (m, 12H, piperazine protons and NHC$\underline{H}$₂CH₂).

EXAMPLE 6

1-[N-(2-phenoxyphenyl)-N-cyclohexylcarbonyl-2-aminoethyl]-4-(2-methoxy phenyl)piperazine The title compound was prepared following the procedure described for the compound in example 4, except that the compound in example 5 was used in place of the compound in example 3, then heated for 2.5 h at reflux. The crude was purified via flash chromatography (EtOAc-petrolium ether 7:3). Yield: 32%.

¹H-NMR (CDCl₃, δ): 7.40–7.20 (m, 4H, aromatics), 7.10 (t, 2H, aromatics), 7.05–6.80 (m, 7H, aromatics), 4.21–4.03 (m, 1H, C(O)NCH($\underline{H}$)CH₂), 3.83 (s, 3H, OCH₃), 3.55–3.40 (m, 1H, C(O)NC($\underline{H}$)HCH₂), 3.10–2.93 (m, 4H, piperazine protons), 2.75–2.50 (m, 6H, piperazine protons and C(O)NCH₂C$\underline{H}$₂), and 2.25–2.05 (m, 1H, CHC(O)), 1.80–0.80 (m, 10H, cyclohexyl protons).

EXAMPLE 7

1-[N-(2-iodophenyl)-2-aminoethyl]-4-(2-methoxyphenyl)piperazine

The title compound was prepared following the procedure described for the compound in example 3, except that 2-iodoaniline was used in place of 2-trifluoromethoxyaniline and heated at 90° C. for 7 h. The crude was purified via flash chromatography (EtOAc-petrolium ether 1:4). Yield: 37%.

¹H-NMR (CDCl₃, δ): 7.65 (dd, 1H, aniline H3), 7.20 (dd, 1H, aniline H5), 7.07–6.80 (m, 4H, methoxyphenyl ring CHs), 6.55 (dd, 1H, aniline H4), 6.45 (dd, 1H, aniline H6), 5.15–5.03 (br, 1H, NH), 3.87 (s, 3H, OCH₃), 3.30–3.05 (m, 6H, piperazine protons and NHC$\underline{H}$₂CH₂), 2.83–2.65 (m, 6H, piperazine protons and NHCH₂C$\underline{H}$₂).

EXAMPLE 8

1-[N-(2-iodophenyl)-N-cyclohexylcarbonyl-2-aminoethyl]-4-(2-methoxyphenyl) piperazine The title compound was prepared following the procedure described for the compound in example 4, except that the compound in example 7 was used in place of the compound in example 3, then heated for 7 h at reflux. Yield: 73%.

$^1$H-NMR (CDCl$_3$, δ): 8.95 (dd, 1H, iodophenyl ring H3), 7.45–7.35 (m, 2H, iodophenyl ring CHs), 7.15–6.80 (m, 5H, methoxyphenyl ring CHs and remaining iodophenyl ring CH), 4.53–4.37 (m, 1H, C(O)NCH(H)CH$_2$), 3.84 (s, 3H, OCH$_3$), 3.20–2.95 (m, 5H, C(O)NC(H)HCH$_2$ and piperazine protons), 2.77–2.50 (m, 7H, C(O)NCH$_2$CH$_2$, piperazine protons and CHC(O)), 1.90–0.80 (m, 10H, cyclohexyl protons).

EXAMPLE 9

1-[N-(2-aminocarbonylphenyl)-2-aminoethyl]-4-(2-methoxyphenyl)piperazine

The title compound was prepared following the procedure described for the compound in example 3, except that 2-aminobenzamide was used in place of 2-trifluoromethoxyaniline. The crude product was purified via flash chromatography (EtOAc) and subsequently crystallized by ethanol. Yield: 36%. Melting point: 134–136° C.

$^1$H-NMR (CDCl$_3$, δ): 8.02–7.85 (br, 1H, NH), 7.41–7.26 (m, 2H, aniline H3,5), 7.05–6.78 (m, 4H, methoxyphenyl ring CHs), 6.73 (dd, 1H, aniline H6), 6.58 (t, 1H, aniline H4), 5.80–5.45 (br, 2H, CONH$_2$), 3.86 (s, 3H, OCH$_3$), 3.33 (t, 2H, NHCH$_2$CH$_2$), 3.20–3.02 (m, 4H, piperazine protons), 2.83–2.62 (m, 6H, NHCH$_2$CH$_2$, and piperazine protons).

EXAMPLE 10

1-[N-(2-cyanophenyl)-2-aminoethyl]-4-(2-methoxyphenyl)piperazine

A mixture containing 0.2 g of the compound in example 9, 0.26 g of triphenylphosphine, 0.08 mL of triethylamine, 0.5 mL of CCl$_4$ and 10 mL of 1,2-dichloroethane was stirred for 3 h at reflux. The residue obtained after evaporation of the solvent was purified via flash chromatography (CH$_2$Cl$_2$—MeOH 98:2) giving 0.14 g (74%) of the title compound.

$^1$H-NMR (CDCl$_3$, δ): 7.40–7.30 (m, 2H, aniline H4,6), 7.05–6.80 (m, 4H, methoxyphenyl ring CHs), 6.70–6.57 (m, 2H, aniline H3,5), 5.45–5.30 (br, 1H, NH), 3.86 (s, 3H, OCH$_3$), 3.25 (q, 2H, NHCH$_2$CH$_2$), 3.20–3.00 (m, 4H, piperazine protons), 2.85–2.60 (m, 6H, NHCH$_2$CH$_2$ and piperazine protons).

EXAMPLE 11

1-[N-(2-acetylphenyl)-2-aminoethyl]-4-(2-methoxyphenyl)piperazine

Preparation of 1-(N-phenyl-2-aminoethyl)-4-(2-methoxyphenyl)piperazine (Compound 11A)

The title compound was prepared following the procedure described for the compound in example 3, except that aniline was used in place of 2-trifluoromethoxyaniline and without solvent. The crude was purified via flash chromatography (petrolium ether-EtOAc 8:2). Yield: 77%.

$^1$H-NMR (CDCl$_3$, δ): 7.30–7.10 (m, 2H, aniline H2,6), 7.10–6.80 (m, 4H, methoxyphenyl ring CHs), 6.80–6.58 (m, 3H, aniline H3,4,5), 4.35 (br, 1H, NH), 3.87 (s, 3H, OCH$_3$), 3.30–3.15 (m, 2H, NHCH$_2$CH$_2$), 3.15–2.98 (m, 4H, piperazine protons), 2.80–2.60 (m, 6H, piperazine protons and NHCH$_2$CH$_2$).

1-[N-(2-acetylphenyl)-2-aminoethyl]-4-(2-methoxyphenyl)piperazine

A solution of 1M boron tribromide in CH$_2$Cl$_2$ (2.37 mL) was dropped into another solution containing 0.74 g of 1-(N-phenyl-2-aminoethyl)-4-(2-methoxyphenyl) piperazine in 10 mL of CH$_2$Cl$_2$ stirred at −3° C. in nitrogen atmosphere. Subsequently, 0.25 mL of acetonitrile at room temperature was added and the mixture was stirred for 1 h at room temperature and for 8 h until precipitation. After cooling at room temperature, the mixture was treated with a 10% aqueous solution of Na$_2$CO$_3$ and the organic phase that separated was dried on anhydrous Na$_2$SO$_4$ and evaporated to dryness. The crude was purified via flash chromatography (CH$_2$Cl$_2$—MeOH 98:2) and the residue crystallized from EtOH giving 0.33 g (39%) of the title compound. Melting point: 92–94° C.

$^1$H-NMR (CDCl$_3$, δ): 9.12–8.95 (br, 1H, NH), 7.75 (dd, 1H, aniline H3), 7.35 (dt, 1H, aniline H5), 7.05–6.80 (m, 4H, methoxyphenyl ring CHs), 6.73 (dd, 1H, aniline H4), 6.58 (dt, 1H, aniline H6), 3.86 (s, 3H, OCH$_3$), 3.35 (q, 2H, NHCH$_2$CH$_2$), 3.20–3.02 (m, 4H, piperazine protons), 2.85–2.61 (m, 6H, NHCH$_2$CH$_2$ and piperazine protons), 2.58 (s, 3H, COCH$_3$).

EXAMPLE 12

1-[N-(2-nitrophenyl)-2-aminoethyl]-4-(4-indolyl)piperazine

A mixture containing 0.49 g of N-(2-chloroethyl)-2-nitroaniline, prepared according to the procedure described by Ramage G. R. et al. in *J. Chem. Soc.* 4406–4409 (1952), 0.55 g of 1-(4-indolyl)piperazine (prepared according to WO 95/33743), 1 mL of triethylamine and 3 mL of DMF was heated at reflux while stirring under nitrogen for 2.5 h. After cooling at room temperature, the mixture was poured into H$_2$O, extracted with CH$_2$Cl$_2$, and the organic phase dried on anhydrous Na$_2$SO$_4$ and evaporated to dryness. The residue was purified via flash chromatography (EtOAc-petrolium ether 3:7) giving 0.35 g (40%) of the title compound.

$^1$H-NMR (CDCl$_3$, δ): 8.60–8.45 (br, 1H, aniline NH), 8.18 (dd, 1H, aniline H3), 8.20–8.10 (br, 1H, indole NH), 7.43 (td, 1H, aniline H5), 7.20–7.05 (m, 3H, indole H3,6,7), 6.85 (dd, 1H, aniline H4), 6.70–6.57 (m, 2H, aniline H6 and indole H5), 6.50 (t, 1H, indole H2), 3.45 (q, 2H, NHCH$_2$CH$_2$), 3.35–3.25 (m, 4H, piperazine protons), 3.85–2.70 (m, 6H, NHCH$_2$CH$_2$ and piperazine protons).

EXAMPLE 13

1-[N-(2-nitrophenyl)-N-cyclohexylcarbonyl-2-aminoethyl]-4-(4-indolyl) piperazine The title compound was prepared according to the procedure described for the compound in example 4, except that the compound in example 12 was used in place of the compound in example 3 and heated for 5 h at reflux. The crude was purified via flash chromatography (EtOAc-petrolium ether 7:3, then only EtOAc was used and at the end only CH$_2$Cl$_2$). Yield: 32%.

$^1$H-NMR (CDCl$_3$, δ): 8.37–8.20 (br, 1H, NH), 8.05 (dd, 1H, nitrophenyl ring H3), 7.65–7.45 (m, 3H, nitrophenyl ring H4,5,6), 7.20–7.00 (m, 3H, indolyle H3,6,7), 6.55 (dd, 1H, indolyle H5), 6.50 (t, 1H, indolyle H2), 4.15–3.95 (m, 1H, C(O)NC(H)CH$_2$), 3.70–3.55 (m, 1H, C(O)NCH(H)CH$_2$), 3.25–2.95 (m, 4H, piperazine protons), 2.75–2.45 (m, 7H, C(O)NCH$_2$CH$_2$, CHC(O), piperazine protons), 2.10–0.80 (m, 10H, cyclohexyl protons).

EXAMPLE 14

1-[N-(2-nitrophenyl)-2-aminoethyl]-4-(2,5-dichlorobenzyl)piperazine

Preparation of 1-(2,5-dichlorobenzyl)-4-ethoxycarbonylpiperazine (Compound 14A)

2,5-Dichlorobenzyl chloride (2.01 g) was added to a mixture of 1.94 g of 1-ethoxycarbonlypiperazine and 3.45 g of anhydrous potassium carbonate in 20 mL of N,N-dimethylformamide stirred at room temperature in nitrogen atmosphere. After 24 h of stirring at the same temperature, the reaction mixture was poured into water and extracted with ethyl acetate. The organic phase, which was dried on anhydrous $Na_2SO_4$, was evaporated to dryness under vacuum. The oily residue was purified via flash chromatography (petrolium ether-ethyl acetate 85::15) giving 2 g (63%) of the title compound.

$^1$H-NMR (CDCl$_3$, δ): 7.50 (d, 1H, aromatic H6), 7.27 (d, 1H, aromatic H3), 7.15 (dd, 1H, aromatic H4), 4.13 (q, 2H, CH$_3$CH$_2$O), 3.58 (s, 2H, benzyl CH$_2$), 3.55–3.45 (m, 4H, piperazine protons), 2.50–2.42 (m, 4H, piperazine protons), 1.26 (t, 3H, CH$_3$CH$_2$O).

Preparation of 1-(2,5-dichlorobenzyl)piperazine
(Compound 14B)

A solution containing 13 g of 1-(2,5-dichlorobenzyl)-4-ethoxycarbonylpiperazine in 35 mL of 37% HCl was stirred for 40 h at reflux. Subsequently, 30 mL of water and 30 mL of EtOAc were added at room temperature, adjusting the pH to 11 via addition of 35% NaOH. The organic phase, which was dried on anhydrous sodium sulphate, was evaporated to dryness under vacuum. The crude was purified via flash chromatography (CHCl$_3$—MeOH 7:3) giving 4.46 g (50%) of the title compound.

$^1$H-NMR (CDCl$_3$, δ): 7.50 (d, 1H, aromatic H6), 7.26 (d, 1H, aromatic H3), 7.14 (dd, 1H, aromatic H4), 3.55 (s, 2H, benzyl CH$_2$), 3.00–2.85 (m, 4H, piperazine protons), 2.55–2.48 (m, 4H, piperazine protons), 1.76 (s, 1H, NH).

Preparation of 1-[N-(2-nitrophenyl)-2-aminoethyl]-4-(2,5-dichlorobenzyl)piperazine This compound was prepared and purified following the method described for the compound in example 12, except that 1-(2,5-dichlorobenzyl)piperazine was used in place of 1-(4-indolyl)piperazine and 4-dimethylaminopyridine was used in place of triethylamine, carrying out the reaction at 120° C. for 8 h. Yield: 35%.

$^1$H-NMR (CDCl$_3$, δ): 8.45 (br, 1H, NH), 8.10 (d, 1H, aniline H3), 7.45 (d, 1H, dichlorophenyl ring H6), 7.38 (dd, 1H, aniline H5), 7.25 (d, 1H, dichlorophenyl ring H3), 7.10 (dd, 1H, dichlorophenyl ring H4), 6.77 (d, 1H, aniline H6), 6.55 (dd, 1H, aniline H4), 3.59 (s, 2H, benzyl CH$_2$), 3.35 (dt, 2H, NHCH$_2$CH$_2$), 2.73 (t, 2H, NHCH$_2$CH$_2$), 2.70–2.38 (m, 8H, piperazine protons).

EXAMPLE 15

1-[N-(2-nitrophenyl)-N-cyclohexylcarbonyl-2-aminoethyl]-4-(2,5-dichlorobenzyl)piperazine The title compound was prepared following the procedure described for the compound in example 2, except that the compound in example 14 was used in place of the compound in example 1 and heated for 12 h at reflux. The crude was purified via flash chromatography (EtOAc-petrolium ether 4:6). Yield: 22%.

$^1$H-NMR (CDCl$_3$, δ): 8.03 (dd, 1H, nitrophenyl ring H3), 7.75–7.40 (m, 4H, dichlorophenyl ring H6 and nitrophenyl ring H4,5,6), 7.25 (d, 1H, dichlorophenyl ring H3), 7.10 (dd, 1H, dichlorophenyl ring H4), 4.05–3.90 (m, 1H, C(O)NCH(H)CH$_2$), 3.65–3.50 (m, 1H, C(O)NC(H)HCH$_2$, 3.52 (s, 2H, benzyl CH$_2$), 2.70–2.20 (m, 10H, C(O)NCH$_2$CH$_2$, piperazine protons), 2.00–0.70 (m, 11H, cyclohexyl protons).

EXAMPLE 16

1-[N-(2-cyclohexylcarbonylaminocarbonylphenyl)-N-cyclohexylcarbonyl-2-aminoethyl]-4-(2-methoxyphenyl)piperazine The title compound was prepared following the procedure described for the compound in example 4, except that the compound in example 9 was used in place of the compound in example 3 and the reaction was carried out for 6 h at reflux in the presence of 2 molar equivalents of cyclohexylcarbonyl chloride. The crude was purified via flash chromatography (CH$_2$Cl$_2$—MeOH 95:5). Yield: 55%.

$^1$H-NMR (DMSO-d$_6$, δ): 12.10–11.80 (br, 1H, NH), 8.08 (dd, 1H, phenylcarbonyl H3), 7.88–7.68 (m, 2H, phenylcarbonyl H5,6), 7.47 (dt, 1H, phenylcarbonyl H4), 7.00–6.80 (m, 4H, methoxyphenyl ring CHs), 4.50–4.33 (m, 2H, C(O)NCH$_2$CH$_2$), 3.75 (s, 3H, OCH$_3$), 3.15—2.85 (m, 5H, CHC(O) and piperazine protons), 2.80–2.68 (m, 2H, C(O)NCH$_2$CH$_2$), 2.68–2.54 (m, 4H, piperazine protons), 2.28–2.08 (m, 1H, CHC(O)), 1.97–1.05 (m, 20H, cyclohexyl protons).

EXAMPLE 17

1-[N-(2-methoxycarbonylphenyl)-2-aminoethyl]-4-(2-methoxyphenyl)piperazine

A mixture of 0.93 g of methyl anthranilate, 2 g of 1-(2-chloroethyl)-4-(2-methoxyphenyl)piperazine, 0.88 g of sodium acetate and 5 mL of H$_2$O was stirred for 24 h at reflux. After cooling at room temperature, the mixture was extracted with EtOAc, the organic phase dried on Na$_2$SO$_4$, evaporated to dryness and the residue purified via flash chromatography (CH$_2$Cl$_2$—MeOH 98:2) giving 0.41 g (18%) of the title compound.

$^1$H-NMR (CDCl$_3$, δ): 7.90 (dd, 1H, aniline H3), 7.90–7.70 (br, 1H, NH), 7.35 (td, 1H, aniline H5), 7.06–6.80 (m, 4H, methoxyphenyl ring CHs), 6.70 (dd, 1H, aniline H6), 6.58 (td, 1H, aniline H4), 3.87 and 3.85 (2s, 6H, COOCH$_3$ and OCH$_3$), 3.43–3.30 (m, 2H, NHCH$_2$CH$_2$), 3.22–3.05 (m, 4H, piperazine protons), 2.83–2.67 (m, 6H, NHCH$_2$CH$_2$ and piperazine protons).

EXAMPLE 18

1-[N-(2-methoxycarbonylphenyl)-N-cyclohexylcarbonyl-2-aminoethyl]-4-(2-methoxyphenyl)piperazine The title compound was prepared following the procedure described for the compound in example 4, except that the compound in example 17 was used in place of the compound in example 3 and the reaction was carried out for 9 h at reflux. The crude was purified by flash chromatography (CH$_2$Cl$_2$—MeOH 95:5). Yield: 38%.

$^1$H-NMR (CDCl$_3$, δ): 8.03 (dd, 1H, methoxycarbonylphenyl ring H3), 7.57 (dt, 1H, methoxycarbonylphenyl ring H4), 7.45 (dt, 1H, methoxycarbonylphenyl ring H5), 7.37 (dd, 1H, methoxycarbonylphenyl ring H6), 7.03–6.80 (m, 4H, methoxyphenyl ring CHs), 4.38–4.15 (m, 1H, C(O)NCH(H)CH$_2$), 3.86 and 3.83 (2s, 6H, COOCH$_3$ and OCH$_3$), 3.33–3.15 (m, 1H C(O)NC(H)HCH$_2$), 3.10–2.93 (m, 4H, piperazine protons), 2.75–2.50 (m, 4H, piperazine protons), 2.56 (t, 2H, C(O)NCH$_2$CH$_2$), 2.00–1.83 (m, 1H, CHC(O)), 1.80–0.80 (m, 10H, cyclohexyl protons).

EXAMPLE 19

1-[N-(2-dimethylaminocarbonylphenyl)-2-aminoethyl]-4-(2-methoxyphenyl) piperazine The title compound was prepared following the procedure described for the compound in example 3, except that N,N-dimethyl-2-aminobenzamide was used in place of 2-trifluoromethoxyaniline. The crude was purified via flash chromatography (EtOAc—MeOH 97:3). Yield: 19%.

¹H-NMR (CDCl₃, δ): 7.25 (dt, 1H, aniline H5), 7.09 (dd, 1H, aniline H3), 7.06–6.80 (m, 4H, methoxyphenyl ring CHs), 6.68 (dd, 1H, aniline H6), 6.66 (dt, 1H, aniline H4), 5.50–5.10 (br, 1H, NH), 3.86 (s, 3H, OCH₃), 3.23 (t, 2H, NHC$\underline{\text{H}}$₂CH₂), 3.18–3.08 (m, 4H, piperazine protons), 3.05 (s, 6H, N(CH₃)₂), 2.78–2.62 (m, 6H, NHCH₂C$\underline{\text{H}}$₂ and piperazine protons).

EXAMPLE 20

1[N-(2-methoxyphenyl)-2-aminoethyl]-4-(2-methoxyphenyl)piperazine

The title compound was prepared and purified following the procedure described for the compound in example 3, except that 2-methoxyaniline was used in place of 2-trifluoromethoxyaniline, and heated at 100° C. for 4 h. Yield: 50%.

¹H-NMR (CDCl₃, δ): 7.05–6.85 (m, 5H, methoxyphenyl ring CHs and aniline CH), 6.85–6.60 (m, 3H, aniline CHs), 3.87 and 3.85 (2s, 6H, 2 OCH₃), 3.25 (t, 2H, NHC$\underline{\text{H}}$₂CH₂), 3.18–3.05 (m, 4H, piperazine protons), 2.80–2.65 (m, 6H, NHCH₂C$\underline{\text{H}}$₂ and piperazine protons).

EXAMPLE 21

1-[N-(2-dimethylaminocarbonylphenyl)-N-cyclohexylcarbonyl-2-aminoethyl]-4-(2-methoxyphenyl)piperazine The title compound was prepared following the procedure described for the compound in example 4, except that the compound in example 19 was used in place of the compound in example 3, 1,2-dichloroethane was used in place of dichloromethane, and the mixture was refluxed for 5 h. The crude was purified by flash chromatography (CH₂Cl₂—MeOH 93:7). Yield: 36%.

¹H-NMR (CDCl₃, δ): 7.50–7.30 (m, 4H, benzamide ring CHs), 7.06–6.80 (m, 4H, methoxyphenyl ring CHs), 4.85 (s, 3H, OCH₃), 4.60–4.40 (m, 1H, CONC$\underline{\text{H}}$(H)CH₂N), 3.67–3.40 (m, 1H, CONCH($\underline{\text{H}}$)CH₂N), 3.35–2.95 (m, 4H, piperazine protons), 3.10 and 2.90 (2s, 6H, N(CH₃)₂), 2.85–2.45 (m, 6H, piperazine protons and CONCH₂C$\underline{\text{H}}$₂N), 2.10–1.90 (m, 1H, CHC(O)), 1.90–0.80 (m, 10H, cyclohexyl protons).

EXAMPLE 22

1-[N-(2-trifluoromethylphenyl)-2-aminoethyl]-4-(2-methoxyphenyl)piperazine

The title compound was prepared following the procedure described for the compound in example 3, except that 2-trifluoromethylaniline was used in place of 2-trifluoromethoxyaniline. The crude was purified via flash chromatography (EtOAc-petroleum ether 2:8). Yield: 14%.

¹H-NMR (CDCl₃, δ): 7.50–7.30 (m, 4H, aniline CHs), 7.10–6.80 (m, 4H, methoxyphenyl ring CHs), 5.50–5.38 (br, 1H, NH), 3.86 (s, 3H, OCH₃), 3.30–3.18 (m, 2H, NHC$\underline{\text{H}}$₂CH₂), 3.18–3.05 (m, 4H, piperazine protons), 2.275 (t, 2H, NHCH₂C$\underline{\text{H}}$₂), 2.80–2.63 (m, 4H, piperazine protons).

EXAMPLE 23

1-[N-(2-methoxyphenyl)-N-cyclohexylcarbonyl-2-aminoethyl]-4-(2-methoxyphenyl)piperazine The title compound was prepared following the procedure described for the compound in example 2, except that the compound in example 20 was used in place of the compound in example 1 and the mixture was refluxed for 6 h. The crude was purified by flash chromatography (CH₂Cl₂—MeOH 9.5:0.5). Yield: 59%.

¹H-NMR (CDCl₃, δ): 7.38 (dd, 1H, methoxyphenylaniline H6), 7.26 (dd, 1H, methoxyphenylaniline H4), 7.10–6.85 (m, 6H, methoxyphenylaniline H3, H5 and methoxyphenyl protons), 4.35–4.12 (m, 1H, CONC$\underline{\text{H}}$(H)CH₂), 3.89 (s, 3H, OCH₃), 3.86 (s, 3H, OCH₃), 3.55–3.33 (m, 1H, CONCH($\underline{\text{H}}$)CH₂), 3.20–2.98 (m, 4H, piperazine protons), 2.80–2.50 (m, 6H, piperazine protons and CONCH₂C$\underline{\text{H}}$₂), 2.05 (tt, 1H, CH C(O)), 1.30–0.85 (m, 10H, cyclohexyl protons).

EXAMPLE 24

1-[N-(2-ethylaminocarbonylphenyl)-2-aminoethyl]-4-(2-methoxyphenyl)piperazine The title compound was prepared following the procedure described for the compound in example 3, except that 2-amino-N-ethylbenzamide was used in place of 2-trifluoromethoxyaniline and the mixture was refluxed for 5 h. The crude was purified by flash chromatography (CH₂Cl₂—MeOH 9.7:0.3). Yield: 12%.

¹H-NMR (CDCl₃, δ): 7.50 (t, 1H, CON$\underline{\text{H}}$Et), 7.38–7.23 (m, 2H, aniline H4, H6), 7.07–6.83 (m, 4H, methoxyphenyl ring CHs), 6.70 (dd, 1H, aniline H3), 6.60 (dd, 1H, aniline H5), 6.13–5.90 (br, 1H, N$\underline{\text{H}}$CH₂CH₂), 3.86 (s, 3H, OCH₃), 3.53–3.40 (m, 2H, CONHC$\underline{\text{H}}$₂CH₃), 3.33 (q, 2H, NHC$\underline{\text{H}}$₂CH₂), 3.18–3.02 (m, 4H, piperazine protons), 2.83–2.63 (m, 6H, piperazine protons and NHCH₂C$\underline{\text{H}}$₂), 1.23 (t, 3H, CONHCH₂C$\underline{\text{H}}$₃).

EXAMPLE 25

1-[N-(2-ethylaminocarbonylphenyl)-N-cyclohexylcarbonyl-2-aminoethyl]-4-(2-methoxyphenyl)piperazine The title compound was prepared following the procedure described for the compound in example 2, except that the compound in example 24 was used in place of the compound in example 1, (toluene instead of 1,2-dichloroethane), and the mixture was refluxed for 12 h. The crude was purified by flash chromatography (CH₂Cl₂—MeOH 9.5:0.5). Yield: 43%.

¹H-NMR (CDCl₃, δ): 9.30–9.12 (br, 1H, CON$\underline{\text{H}}$Et), 7.80 (dd, 1H, aniline H6), 7.45 (dd, 1H, aniline H4), 7.35 (dd, 1H, aniline H5), 7.20 (dd, 1H, aniline H3), 7.05–6.75 (m, 4H, methoxyphenyl ring CHs), 4.47 (dt, 1H, CONC$\underline{\text{H}}$(H)CH₂N), 3.82 (s, 3H, OCH₃), 3.73–3.50 (m, 1H, CONHC$\underline{\text{H}}$(H)CH₃), 3.32–3.10 (m, 1H, CONHC$\underline{\text{H}}$(H)CH₃), 3.03–2.25 (m, 5H, CONC$\underline{\text{H}}$(H)CH₂N and piperazine protons), 2.65–2.16 (m, 7H, CONCH₂C$\underline{\text{H}}$₂, piperazine protons and CHC(O)), 1.70–0.80 (m, 10H, cyclohexyl protons), 1.18 (t, 3H, CONHCH₂C$\underline{\text{H}}$₃).

EXAMPLE 26

1-[N-(2-trifluoromethylphenyl)-N-cyclohexylcarbonyl-2-aminoethyl]-4-(2-methoxyphenyl)piperazine Preparation of N-(2-trifluoromethylphenyl) cyclohexanecarboxamide (Compound 26A)

A solution of 2-trifluoromethylaniline (3 mL), triethylamine (3.5 mL) and CH₂Cl₂ (30 mL) was stirred at room temperature under $N_2$ and added dropwise with cyclohexanecarbonyl chloride (3.34 mL). After 2.5 h stirring at room temperature, the mixture was poured into $H_2O$ and alkalinized with 1 N NaOH. The organic phase was dried on anhydrous $Na_2SO_4$ and the crude was crystallized from EtOH to give 3.82 g (59%) of the title compound. M.p. 153–154° C.

$^1$H-NMR (CDCl$_3$, δ): 8.20 (dd, 1H, trifluoromethylphenyl ring CH), 7.60–7.40 (m, 3H, trifluoromethylphenyl ring CHs and NH), 7.12 (ddd, 1H, trifluoromethylphenyl ring CH), 2.230 (tt, 1H, CHC(O)), 2.10–1.20 (m, 10H, cyclohexyl protons).

Preparation of 1-[N-(2-trifluoromethylphenyl)-N-cyclohexylcarbonyl-2-aminoethyl]-4-(2-methoxyphenyl)piperazine A mixture of N-(2-trifluoromethylphenyl) cyclohexanecarboxamide (0.2 g) (compd 26A), 1-(2-chloroethyl)-4-(2-methoxyphenyl)piperazine (0.37 g), 50% (w/w) NaOH (0.5 mL), TEBAC (0.16 g) and toluene (2 mL) was stirred at 80° C. for 3.5 h. An additional amount of compd 26A (0.2 g) was then added and after 6 h stirring at 80° C. The mixture was poured into $H_2O$ and extracted with $CH_2Cl_2$. The organic phase was dried on anhydrous $Na_2SO_4$, evaporated to dryness and the residue purified by flash chromatography (EtOAc-petroleum ether 3:7) giving 0.12 g (17%) of the title compound.

$^1$H-NMR (CDCl$_3$, δ): 7.77 (dd, 1H, trifluoromethylphenyl ring CH), 7.70–7.45 (m, 3H, trifluoromethylphenyl ring CHs), 7.10–6.80 (m, 4H, methoxyphenyl ring CHs), 4.70–4.50 (m, 1H, CONCH(H)CH$_2$N), 3.85 (s, 3H, OCH$_3$), 3.20–2.90 (m, 5H, CONCH(H)CH$_2$N and piperazine protons), 2.85–2.45 (m, 7H, CHC(O), CONCH$_2$CH$_2$N and piperazine protons), 1.90–0.75 (m, 10H, cyclohexyl protons).

EXAMPLE 27

1-[N-(2-aminophenyl)-N-cyclohexylcarbonyl-2-aminoethyl]-4-(2-methoxyphenyl)piperazine A mixture of 1.05 g of the compound in example 2, 2 mL of hydrazine .H$_2$O and 1 g of Raney nickel in 70 mL of MeOH was stirred at 50° C. for 1.5 h. The insoluble was separated by filtration and the solution was evaporated to dryness. The residue was crystallized from EtOH to give 0.69 g (71%) of the title compound. Melting point: 138.5–140° C.

$^1$H-NMR (CDCl$_3$, δ): 7.15 (dd, 1H, aminophenyl ring CH), 7.10–6.80 (m, 5H, aminophenyl ring CH and methoxyphenyl ring CHs), 6.80–6.65 (m, 2H, aminophenyl ring CHs), 4.96 (s, 2H, NH$_2$), 4.96–4.65 (m, 1H, CONCH(H)CH$_2$N), 3.86 (s, 3H, OCH$_3$), 3.20–2.80 (m, 7H, CONCH(H)CH$_2$N and piperazine protons), 2.45–2.65 (m, 4H, piperazine protons), 2.10 (tt, 1H, CH(O)), 1.90–0.80 (m, 10H, cyclohexyl protons).

EXAMPLE 28

1-[N-(2-acetylaminophenyl)-N-cyclohexylcarbonyl-2-aminoethyl]-4-(2-methoxyphenyl)piperazine To a stirred solution of 0.22 g of the compound described in example 27 and 0.08 mL of triethylamine in 5 mL of $CH_2Cl_2$ was added a solution of 0.04 mL of acetyl chloride in 0.5 mL $CH_2Cl_2$ at room temperature. After 2 h stirring at the same temperature, the solvent was evaporated to dryness and the residue purified by flash chromatography ($CH_2Cl_2$—$CH_3CN$ 98:2) to give 0.12 g (50%) of the title compound.

$^1$H-NMR (CDCl$_3$, δ): 9.90 (s, 1H, NH), 7.85 (dd, 1H, acetylaminophenyl ring CH), 7.40 (td, 1H, acetylaminophenyl ring CH), 7.23–7.10 (m, 2H, acetylaminophenyl ring CHs), 7.05–6.80 (m, 4H, methoxyphenyl ring CHs), 5.00–4.80 (m, 1H, CONCH(H)CH$_2$N), 3.83 (s, 3H, OCH$_3$), 3.20–2.25 (m, 11H, CONCH(H)CH$_2$N and piperazine protons), 2.15 (s, 3H, COCH$_3$), 2.05–1.85 (m, 1H, CHC(O)), 1.75–0.80 (m, 10H, cyclohexyl protons).

EXAMPLE 29

1-[N-(2-nitrophenyl)-N-cyclohexylcarbonyl-2-aminoethyl]-4-(2-methoxyphenyl)piperazine $N^1$-oxide A suspension of 0.89 g of 83% magnesium monoperoxyphthalate .0.6 $H_2O$ in 10 mL of $H_2O$ was added dropwise into a solution of 1.4 g of the compound described in example 2 in 10 mL of CHCl$_3$ and 45 mL of MeOH at 5° C.

After overnight resting at room temperature, the solvents were evaporated to dryness and the residue was treated with 50 mL of $H_2O$, alkalinized with 20% $Na_2CO_3$ and extracted with CHCl$_3$. The organic phase was dried on anhydrous $Na_2SO_4$ and evaporated to dryness. The residue was purified by flash chromatography (CHCl$_3$-2 N methanolic NH$_3$ gradient 100:7 to 100:20) to give 0.5 g of a crude, that was crystallized from Me$_2$CO yielding 0.35 g (24%) of the title compound. Melting point: 128–132° C.

$^1$H-NMR (CDCl$_3$, δ): 8.05 (dd, 1H, nitrophenyl ring H3), 7.70 (ddd, 1H, nitrophenyl ring H5), 7.50 (ddd, 1H, nitrophenyl ring H4), 7.41 (dd, 1H, nitrophenyl ring H6), 7.07–6.76 (m, 4H, methoxyphenyl ring CHs), 4.40–4.12 (m, 2H, CONCH$_2$CH$_2$N), 3.85 (s, 3H, OCH$_3$), 3.70–3.35 (m, 6H, CONCH$_2$CH$_2$N and piperazine protons), 3.35–3.07 (m, 4H, piperazine protons), 2.05–1.80 (m, 1H, CHC(O)), 1.75–0.75 (m, 10H, cyclohexyl protons).

EXAMPLE 30

1-[N-(2-nitrophenyl)-N-cyclohexylcarbonyl-2-aminoethyl]-4-(2-methoxyphenyl)piperazine $N^4$-oxide The title compound was isolated during purification of the compound described in example 29. Yield 0.23 g (16%) as a vitreous solid.

$^1$H-NMR (CDCl$_3$, δ): 8.75 (dd, 1H, methoxyphenyl ring H6), 8.05 (dd, 1H, nitrophenyl ring H3), 7.71 (ddd, 1H, nitrophenyl ring H5), 7.57 (ddd, 1H, nitrophenyl ring H4), 7.47 (dd, 1H, nitrophenyl ring H6), 7.37 (ddd, 1H, methoxyphenyl ring H4 (H5)), 7.10 (ddd, 1H, methoxyphenyl ring H5 (H4)), 6.98 (dd, 1H, methoxyphenyl ring H3), 4.72–4.41 (m, 2H, piperazine protons), 4.03 (s, 3H, OCH$_3$), 3.83 (t, 2H, CONCH$_2$CH$_2$N), 3.35–3.09 (m, 2H, piperazine protons), 2.98–2.77 (m, 2H, CONCH$_2$CH$_2$N), 2.77–2.30 (m, 4H, piperazine protons), 2.05–0.83 (m, 11H, cyclohexyl protons).

EXAMPLE 31

1-[N-(2-nitrophenyl)-N-cyclohexylcarbonyl-2-aminoethyl]-4-(2-methoxyphenyl)piperazine $N^1,N^4$-dioxide The title compound was synthesized as described for example 29 but using equimolar amounts of magnesium monoperoxyphthalate and compound described in example 2. Yield 43% after crystallization from CH$_3$CN. Melting point: 153–157° C.

¹H-NMR (CDCl₃, δ): 8.70 (dd, 1H, methoxyphenyl ring H6), 8.05 (dd, 1H, nitrophenyl ring H3), 7.70 (ddd, 1H, nitrophenyl ring H5), 7.58 (ddd, 1H, nitrophenyl ring H4), 7.49–7.32 (m, 2H, nitrophenyl ring H6 and methoxyphenyl ring H4), 7.13 (ddd, 1H, methoxyphenyl ring H5), 7.00 (dd, 1H, methoxxyphenyl ring H3), 5.92–5.67 (m, 2H, piperazine protons), 4.70–4.45 (m, 2H, piperazine protons), 4.45–4.05 (m, 2H, CONCH₂CH₂N), 4.00 (s, 2H, CONCH₂CH₂N), 3.30–3.08 (m, 2H, piperazine protons), 3.05–2.85 (m, 2H, piperazine protons), 2.05–1.78 (m, 1H, CHC(O)), 1.78–0.70 (m, 10H, cyclohexyl protons).

EXAMPLE 32

1-[N-(2-nitrophenyl)-N-(3-furylcarbonyl)-2-aminoethyl]-4-(2-methoxyphenyl)piperazine A suspension of 0.77 g of the monohydrochloride of compound described in example 1 in 50 mL of toluene was stirred at reflux removing about 20 mL of distillate. After cooling to 60–70° C., 0.9 mL of 97% diisopropylethylamine (DIPEA) was added and the mixture stirred for 15'.0.66 g of 3-furylcarbonyl chloride was then added to the mixture that was stirred at reflux for 5 h, cooled to room temperature, washed in the sequence with H₂O, 1 N NaOH and H₂O, dried on anhydrous Na₂SO₄ and evaporated to dryness. The residue was purified by flash chromatography (EtOAc-petroleum ether gradient 1:1 to 7:3) affording 0.67 g (75%) of the title compound.

¹H-NMR (CDCl₃, δ): 8.05 (dd, 1H, nitrophenyl ring H3), 7.73–7.58 (m, 2H, nitrophenyl ring H5 and H6), 7.58–7.45 (m, 1H, nitrophenyl ring H4), 7.15 (br, 1H, furan ring H2), 7.02–6.77 (m, 5H, furan ring H5 and methoxyphenyl ring CHs), 6.13 (br, 1H, furan ring H4), 4.30–4.08 (m, 1H, CONCH(H)CH₂N), 3.90–3.70 (m, 1H, CONCH(H)CH₂N), 3.83 (s, 3H, OCH₃), 3.05–2.80 (m, 4H, piperazine protons), 2.80–2.62 (m, 2H, CONCH₂CH₂N), 2.62–2.45 (m, 4H, piperazine protons).

EXAMPLE 33

1-[N-(2-nitrophenyl)-N-(2-furylcarbonyl)-2-aminoethyl]-4-(2-methoxyphenyl)piperazine The title compound was prepared following the procedure described for the compound in example 32, except that 2-furylcarbonyl chloride was used in place of 3-furancarbonyl chloride. Yield 77%.

¹H-NMR (CDCl₃, δ): 8.05 (dd, 1H, nitrophenyl ring H3), 7.72–7.45 (m, 3H, other nitrophenyl ring CHs), 7.20 (br, 1H, furan ring H3), 7.05–6.75 (m, 4H, methoxyphenyl ring CHs), 6.49 (br, 1H, furan ring H4), 6.25 (br, 1H, furan ring H5), 4.30–4.10 (m, 1H, CONCH(H)CH₂N), 3.98–3.75 (m, 1H, CONCH(H)CH₂N), 3.83 (s, 3H, OCH₃), 3.15–2.85 (m, 4H, piperazine protons), 2.85–2.65 (m, 2H, CONCH₂CH₂N), 2.65–2.48 (m, 4H, piperazine protons).

EXAMPLE 34

1-[N-(2-nitrophenyl)-N-(2-thiophenecarbonyl)-2-aminoethyl]-4-(2-methoxyphenyl)piperazine The title compound was prepared following the procedure described for the compound in example 32, except that 2-thiophenecarbonyl chloride was used in place of 3-furylcarbonyl chloride and reflux lasted 8 h. Yield 59%.

¹H-NMR (CDCl₃, δ): 8.03 (dd, 1H, nitrophenyl ring H3), 7.71–7.60 (m, 2H, nitrophenyl ring H5 and H6), 7.60–7.45 (m, 1H, nitrophenyl ring H4), 7.27 (dd, 1H, thiophene ring H3 (H5)), 7.05–6.70 (m, 6H, thiophene H4 and H5 (H3) and methoxyphenyl ring CHs), 4.22–4.10 (m, 1H, CONCH(H)CH₂N), 3.92–3.71 (m, 1H, CONCH(H)CH₂N), 3.80 (s, 3H,OCH₃), 3.10–2.80 (m, 4H, piperazine protons), 2.80–2.65 (m, 2H, CONCH₂CH₂N), 2.65–2.45 (m, 4H, piperazine protons).

EXAMPLE 35

1-[N-(2-nitrophenyl)-N-(3-thiophenecarbonyl)-2-aminoethyl]-4-(2-methoxy phenyl)piperazine The title compound was prepared following the procedure described for the compound in example 32, except that 3-thiophenecarbonyl chloride was used in place of 3-furylcarbonyl chloride and reflux lasted 7 h. Yield 88%.

¹H-NMR (CDCl₃, δ): 7.93 (dd, 1H, nitrophenyl ring H3), 7.70–7.55 (m, 2H, nitrophenyl ring H5 and H6), 7.48–7.35 (m, 1H, nitrophenyl ring H4), 7.25–7.12 (m, 1H, thiophene ring H2), 7.12–7.02 (m, 1H, thiophene ring H5) 7.02–6.91 (m, 1H, thiophene ring H4), 6.91–6.78 (m, 4H, methoxyphenyl ring CHs), 4.32–4.10 (m, 1H, CONCH(H)CH₂N), 3.90–3.70 (m, 1H, CONCH(H)CH₂N), 3.81 (s, 3H,OCH₃), 3.05–2.78 (m, 4H, piperazine protons), 2.78–2.65 (m, 2H, CONCH₂CH₂N), 2.65–2.45 (m, 4H, piperazine protons).

EXAMPLE 36

1-[N-(2-nitrophenyl)-N-(4-pyridylcarbonyl)-2-aminoethyl]-4-(2-methoxyphenyl) piperazine The title compound was prepared following the procedure described for the compound in example 32, except that 4-pyridylcarbonyl chloride was used in place of 3-furylcarbonyl chloride and reflux lasted 14 h. The crude was purified by flash chromatography (CHCl₃—2.5 N methanolic NH₃ gradient 100:1.5 to 100:3). Yield 39%.

¹H-NMR (CDCl₃, δ): 8.42 (dd, 2H, pyridine ring H2 and H6), 7.90 (dd, 1H, nitrophenyl ring H3), 7.62–7.45 (m, 2H, nitrophenyl ring H5 and H6), 7.45–7.30 (m, 1H, nitrophenyl ring H4), 7.15 (dd, 2H, pyridine ring H3 and H5) 7.08–6.75 (m, 4H, methoxyphenyl ring CHs), 4.50–4.20 (m, 1H, CONCH(H)CH₂N), 3.90–3.65 (m, 1H, CONCH(H)CH₂N), 3.80 (s, 3H,OCH₃), 3.15–2.28 (m, 10H, CONCH₂CH₂N and piperazine protons).

EXAMPLE 37

1-[N-(2-nitrophenyl)-N-(3-pyridylcarbonyl)-2-aminoethyl]-4-(2-methoxyphenyl)piperazine The title compound was prepared following the procedure described for the compound in example 32, except that 3-pyridylcarbonyl chloride was used in place of 3-furylcarbonyl chloride and reflux lasted 12 h. The crude was purified by flash chromatography (CHCl₃—2.5 N methanolic NH₃ 100:3). Yield 46%.

¹H-NMR (CDCl₃, δ): 8.50–8.35 (m, 2H, pyridine ring H2 and H6), 7.90 (dd, 1H, nitrophenyl ring H3), 7.72 (dd, 1H, pyridine ring H4), 7.60–7.50 (m, 2H, nitrophenyl ring H5 and H6), 7.43–7.28 (m, 1H, nitrophenyl ring H4) 7.30–7.15 (m, 1H, pyridine ring H5), 7.03–6.76 (m, 4H, methoxyphenyl ring CHs), 4.35–4.15 (m, 1H, CONCH(H)CH₂N), 4.00–3.75 (m, 1H, CONCH(H)CH₂N), 3.80 (s, 3H,OCH₃), 3.10–2.40 (m, 10H, CONCH₂CH₂N and piperazine protons).

EXAMPLE 38

1-[N-(2-nitrophenyl)-N-(2-pyrazinylcarbonyl)-2-aminoethyl]-4-(2-methoxy phenyl)piperazine The title compound was prepared following the procedure described for the compound in example 32, except that 2-pyrazinylcarbonyl chloride was used in place of 3-furylcarbonyl chloride and reflux lasted 1 h. The crude was purified by flash chromatography (CHCl$_3$—2.5 N methanolic NH$_3$ gradient 100:1 to 100:3). Yield 89%.

$^1$H-NMR (CDCl$_3$, δ): 9.08 (d, 1H, pyrazine ring H3), 8.40 (d, 1H, pyrazine ring H6), 8.07 (d, 1H, pyrazine ring H5), 7.97 (dd, 1H, nitrophenyl ring H3), 7.62–7.50 (m, 2H, nitrophenyl ring H5 and H6) 7.48–7.31 (m, 1H, nitrophenyl ring H4), 7.05–6.80 (m, 4H, methoxyphenyl ring CHs), 4.31–4.15 (m, 1H, CONCH(H)CH$_2$N), 4.08–3.92 (m, 1H, CONCH(H)CH$_2$N), 3.82 (s, 3H,OCH$_3$), 3.05–2.40 (m, 10H, CONCH$_2$CH$_2$N and piperazine protons).

EXAMPLE 39

1-[N-(2-nitrophenyl)-N-(1-methylcyclohexylcarbonyl)-2-aminoethyl]-4-(2-methoxy phenyl)piperazine Preparation of 1-methyl-N-(2-nitrophenyl)cyclohexanecarboxamide (Compound 39A)

This compound was prepared following the procedure described for compound 26A in example 26, except that 1-methylcyclohexanecarbonyl chloride (J. Org. Chem. 47, 3242 (1982)) was used in place of cyclohexanecarbonyl chloride and the reaction mixture was refluxed for 50 h. The crude was purified by flash chromatography (petroleum ether-EtOAc 100:2). Yield 90%.

$^1$H-NMR (CDCl$_3$, δ): 10.75 (s, 1H, NH), 8.85 (dd, 1H, nitrophenyl ring H6), 8.22 (dd, 1H, nitrophenyl ring H3), 7.62 (ddd, 1H, nitrophenyl ring H5), 7.15 (ddd, 1H, nitrophenyl ring H4) 2.20–1.95 (m, 2H, cyclohexyl protons), 1.75–1.35 (m, 8H, cyclohexyl protons), 1.25 (s, 3H, CH$_3$).

Preparation of 1-[N-(2-nitrophenyl)-N-(1-methylcyclohexylcarbonyl)-2-aminoethyl]-4-(2-methoxyphenyl)piperazine A mixture of 0.3 g of 1-methyl-N-(2-nitrophenyl)cyclohexanecarboxamide (compound 39A), 50 mL of toluene and 0.26 g of tert-BuOK was stirred at reflux removing about 11 mL of distillate, then a solution of 0.32 g of 1-(2-chloroethyl)-4-(2-methoxyphenyl)piperazine in 10 mL of toluene was added to the mixture. After 16 h stirring at reflux, the mixture was cooled and washed with H$_2$O, the organic layer was dried on anhydrous Na$_2$SO$_4$ and evaporated to dryness. The crude was purified by flash chromatography (petroleum ether-EtOAc 7:3) to give 0.51 g (43%) of the title compound.

$^1$H-NMR (CDCl$_3$, δ): 7.98 (dd, 1H, nitrophenyl ring H3), 7.40 (ddd, 1H, nitrophenyl ring H5), 7.08–6.80 (m, 6H, nitrophenyl ring H4 and H6 and methoxyphenyl ring CHs), 4.31–4.10 (m, 2H, CONCH$_2$CH$_2$), 3.85 (s, 3H, OCH$_3$), 3.20–2.98 (m, 4H, piperazine protons), 2.88–2.62 (m, 6H, CONCH$_2$CH$_2$ and piperazine protons), 1.90–1.70 (m, 2H, cyclohexyl protons), 1.53–1.22 (m, 8H, cyclohexyl protons), 1.18 (s, 3H, CH$_3$).

EXAMPLE 40

1-[N-(2-nitrophenyl)-N-(1-phenylcyclohexylcarbonyl)-2-aminoethyl]-4-(2-methoxyphenyl)piperazine Preparation of 1-phenyl-N-(2-nitrophenyl)cyclohexanecarboxamide (Compound 40A)

This compound was prepared following the procedure described for compound 39A in example 39, except that 1-phenylcyclohexanecarbonyl chloride (J. Am. Chem. Soc. 68, 2345-7 (1946)) was used in place of 1-methylcyclohexanecarbonyl chloride, toluene in place of CH$_2$Cl$_2$, DIPEA in place of triethylamine and reaction mixture was refluxed for 15 h. The crude was purified by flash chromatography (petroleum ether-EtOAc 98:2). Yield 91%.

$^1$H-NMR (CDCl$_3$, δ): 10.32 (s, 1H, NH), 8.76 (dd, 1H, nitrophenyl ring H6), 8.12 (dd, 1H, nitrophenyl ring H3), 7.64–7.32 (m, 5H, phenyl ring CHs), 7.28 (ddd, 1H, nitrophenyl ring H5), 7.08 (ddd, 1H, nitrophenyl ring H4), 2.54–2.34 (m, 2H, cyclohexyl protons), 2.22–2.02 (m, 2H, cyclohexyl protons), 1.76–1.28 (m, 6H, cyclohexyl protons).

Preparation of 1-[N-(2-nitrophenyl)-N-(1-phenylcyclohexylcarbonyl)-2-aminoethyl]-4-(2-methoxyphenyl)piperazine The title compound was prepared following the procedure described for compound in example 39, except that compound 40A was used in place of 1-methyl-N-(2-nitrophenyl)cyclohexanecarboxamide and reflux lasted 22 h. The crude was purified by flash chromatography (petroleum ether-EtOAc gradient 8:2 to 7:3). Yield 37%.

$^1$H-NMR (CDCl$_3$, δ): 7.90 (dd, 1H, nitrophenyl ring H3), 7.45–7.10 (m, 7H, phenyl ring CHs and nitrophenyl ring H5 and H6), 7.04–6.78 (m, 5H, nitrophenyl ring H4 and methoxyphenyl ring CHs), 4.30–4.12 (m, 2H, CONCH$_2$CH$_2$), 3.82 (s, 3H, OCH$_3$), 3.18–2.93 (m, 4H, piperazine protons), 2.80–2.50 (m, 6H, CONCH$_2$CH$_2$ and piperazine protons), 2.30–2.10 (m, 2H, cyclohexyl protons), 1.92–1.75 (m, 2H, cyclohexyl protons), 1.74–1.35 (m, 6H, cyclohexyl protons).

EXAMPLE 41

1-[N-[2-(2,2,2-trifluoroethoxy)phenyl]-2-aminoethyl]-4-(2-methoxyphenyl) piperazine The title compound was prepared following the procedure described for compound in example 3, except that 2-(2,2,2-trifluoroethoxy)aniline (EP 748800) was used in place of 2-trifluoromethoxyaniline and the reaction mixture was refluxed for 7 h. The crude was purified by flash chromatography (petroleum ether-EtOAc gradient 9:1 to 8:2). Yield 38%.

$^1$H-NMR (CDCl$_3$, δ): 7.08–6.80 (m, 5H, methoxyphenyl ring CHs and trifluoroethoxyphenyl ring CH), 6.80–6.57 (m, 3H, trifluroethoxyphenyl ring CHs), 5.11–4.70 (m, 1H, NH), 4.35 (q, 2H, OCH$_2$CF$_3$), 3.85 (s, 3H, OCH$_3$), 3.38–3.19 (m, 2H, NHCH$_2$CH$_2$), 3.19–2.98 (m, 4H, piperazine protons), 2.88–2.60 (m, 6H, NHCH$_2$CH$_2$ and piperazine protons).

EXAMPLE 42

1-[N-[2-(2,2,2-trifluoroethoxy)phenyl]-N-cyclohexylcarbonyl-2-aminoethyl]-4-(2-methoxyphenyl)piperazine A mixture of 0.41 g of the compound described in example 41, 5.4 mL of 97% DIPEA, 3.9 mL of cyclohexanecarbonyl chloride in 30 mL of toluene was stirred at reflux for 10 h. After cooling to room temperature, the mixture was washed in the sequence with H$_2$O, 1 N NaOH and H$_2$O, the organic layer was dried on anhydrous Na$_2$SO$_4$ and evaporated to dryness. The crude was purified by flash chromatography (petroleum ether-EtOAc 1:1) followed by crystallization from Et$_2$O to give 0.2 g (37%) of the title compound. Melting point: 109.6–112° C.

$^1$H-NMR (CDCl$_3$, δ): 7.42–7.22 (m, 2H, trifluoroethoxyphenyl ring CHs), 7.15–6.77 (m, 6H, trifluoroethoxyphenyl ring CHs and methoxyphenyl ring CHs), 4.38 (q, 2H, OCH$_2$CF$_3$), 4.22–402 (m, 1H, CONCH(H)CH$_2$N), 3.82 (s, 3H, OCH$_3$), 3.58–3.39 (m, 1H, CONCH(H)CH$_2$N), 3.15–2.90 (m, 4H, piperazine protons), 2.80–2.45 (m, 6H, CONCH$_2$CH$_2$N and piperazine protons), 2.05–1.88 (m, 1H, CHC(O)), 1.75–0.80 (m, 10H, cyclohexyl protons).

EXAMPLE 43

1-[N-(2-cyanophenyl)-N-cyclohexylcarbonyl-2-aminoethyl]-4-(2-methoxy phenyl)piperazine hydrochloride Preparation of N-(2-cyanophenyl)cyclohexanecarboxamide (Compound 43A)

This compound was prepared following the procedure described for compound 26A in example 26, except that 2-cyanoaniline was used in place of 2-trifluoromethylaniline. Yield 75%. M.p. 135–137° C.

$^1$H-NMR (CDCl$_3$, δ): 8.40 (dd, 1H, cyanophenyl ring H3), 7.70–7.50 (m, 3H, cyanophenyl ring H5 and H6 and NH), 7.12 (ddd, 1H, cyanophenyl ring H4), 2.30 (tt, 1H, CHC(O)), 2.05–1.10 (m, 10H, cyclohexyl protons).

Preparation of 1-[N-(2-cyanophenyl)-N-cyclohexylcarbonyl-2-aminoethyl]-4-(2-methoxyphenyl)piperazine hydrochloride The title compound was prepared following the procedure described for compound in example 39, except that compound 42A was used in place of compound 39A and reflux lasted 1 h. The crude was purified by flash chromatography (CH$_2$Cl$_2$—MeOH 98:2). The residue was dissolved in Me$_2$CO, added with HCl in Et$_2$O, evaporated to dryness, and crystallized from Me$_2$CO+Et$_2$O to give the title compound. Yield 7%.

$^1$H-NMR (DMSO-d$_6$, δ): 11.28–11.07 (br, 1H, NH$^+$), 8.05 (dd, 1H, cyanophenyl ring H6), 7.92–7.80 (m, 2H, cyanophenyl ring CHs), 7.72–7.60 (m, 1H, cyanophenyl ring CH), 7.05–6.82 (m, 4H, methoxyphenyl ring CHs), 4.45–4.30 (m, 1H, CONCH(H)CH$_2$N), 3.92–3.75 (m, 1H, CONCH(H)CH$_2$N), 3.80 (s, 3H, OCH$_3$), 3.70–3.40 (m, 4H, piperazine protons), 3.40–3.00 (m, 6H, CONCH$_2$CH$_2$N and piperazine protons), 1.98–1.80 (m, 1H, CHC(O)), 1.80–0.75 (m, 10H, cyclohexyl protons).

EXAMPLE 44

1-[N-(2-nitrophenyl)-1-amino-2-propyl]-4-(2-methoxyphenyl)piperazine

Preparation of 2-[4-(2-methoxyphenyl)-1-piperazinyl]propionamide (Compound 44A)

A mixture of 1 g of 1-(2-methoxyphenyl)piperazine, 0.57 g of 2-chloropropionamide, 1 mL of DIPEA and 5 mL of toluene was stirred at reflux for 3 h under N$_2$. After cooling to room temperature the mixture was poured into H$_2$O, extracted with EtOAc, then the organic layer was dried on Na$_2$SO$_4$ and the solvents evaporated to dryness. The residue was purified by flash chromatography (CH$_2$Cl$_2$—2 N methanolic ammonia 95:5) to give 0.88 g (63%) of compound 44A.

$^1$H-NMR (CDCl$_3$, δ): 7.25–7.10 (br, 1H, CONH(H)), 7.10–6.80 (m, 4H, methoxyphenyl ring CHs), 5.75–5.60 (br, 1H, CONH(H)), 3.85 (s, 3H, OCH$_3$), 3.20–3.00 (m, 4H, piperazine protons, NCH(CH$_3$)CO), 2.85–2.60 (m, 4H, piperazine protons), 1.30 (d, 3H, NCH(CH$_3$)CO).

Preparation of 2-[4-(2-methoxyphenyl)-1-piperazine]propanamine (Compound 44B)

To a solution of 0.28 g of compound 44A in 7 mL of THF stirred at –4° C. under N$_2$ was added dropwise 2 mL of a 2 M THF solution of diborane dimethylsulfide. The mixture was refluxed for 6.5 h then 3 mL oh MeOH was added and the solvents evaporated to dryness. The residue was treated with water and extracted with EtOAc, the organic phase dried on Na$_2$SO$_4$ and evaporated to dryness, the residue was purified by flash chromatography (CH$_2$Cl$_2$—2 N methanolic ammonia 95:5) to give 0.07 g (24%) of compound 44B.

$^1$H-NMR (CDCl$_3$, δ): 7.10–6.80 (m, 4H, methoxyphenyl ring CHs), 3.85 (s, 3H, OCH$_3$), 3.20–2.90 (m, 4H, piperazine protons), 2.85–2.50 (m, 7H, piperazine protons and NCH(CH$_3$)CH$_2$), 2.05–1.85 (br, 2H, NH$_2$), 0.95 (d, 3H, CH$_3$).

Preparation of 1-[N-(2-nitrophenyl)-1-amino-2-propyl]-4-(2-methoxyphenyl)piperazine A mixture of 0.08 g of compound 44B, 0.03 mL of 2-nitrofluorobenzene, 0.3 mL of DIPEA and 5 mL of DMF was stirred at 140° C. for 3 h under N$_2$. The cooled mixture was diluted with water and extranced with diethyl ether; the organic phase was dried on Na$_2$SO$_4$, evaporated to dryness and the residue purified by flash chromatography (petroleum ether-EtOAc 8:2) to give 0.07 g (62%) of the title compound.

$^1$H-NMR (CDCl$_3$, δ): 8.90–8.70 (br, 1H, NH), 8.15 (dd, 1H, nitrophenyl ring H3), 7.40 (ddd, 1H, nitrophenyl ring H5), 7.15–6.70 (m, 5H, nitrophenyl ring H6 and methoxyphenyl ring CHs), 6.63 (ddd, 1H, nitrophenyl ring H4), 3.85 (s, 3H, OCH$_3$), 3.70–2.60 (m, 11H, piperazine protons and NHCH$_2$CH(CH$_3$)), 1.10 (d, 3H, CH$_3$).

EXAMPLE 45

1-[N-(2-nitrophenyl)-N-cyclohexylcarbonyl-1-amino-2-propryl]-4-(2-methoxyphenyl)piperazine The title compound was prepared following the procedure described for the compound in example 4, except that the compound in example 44 was used in place of the compound in example 3, toluene was used instead of 1,2-dichloroethane and reflux lasted 13 h. The mixture was purified by flash chromatography (petroleum ether-EtOAc 1:1). Yield 61%.

$^1$H-NMR (CDCl$_3$, δ): 8.05 (dd, 1H, nitrophenyl ring H3), 7.85–7.45 (m, 3H, nitrophenyl ring H4, H5 and H6), 7.10–6.75 (m, 4H, methoxyphenyl ring CHs), 3.85 (s, 3H, OCH$_3$), 3.90–3.75 (m, 1H, CONCH(H)CH(CH$_3$)), 3.65–2.30 (m, 10H, piperazine protons and CONCH(H)CH(CH$_3$)), 2.10–1.80 (m, 1H, CHC(O)), 1.80–0.80 (m, 13H, cyclohexyl protons and CH$_3$).

EXAMPLE 46

Effects on Volume-Induced Rhythmic Bladder Voiding Contractions in Anaesthetized Rats A. Methods:

Female Sprague Dawley rats weighing 225–275 g (Crl: CDo BR, Charles River Italia) were used. The animals were housed with free access to food and water and were maintained on a forced 12 h alternating light-dark cycle at 22–24° C. for at least one week, except during the experiment. The activity on the rhythmic bladder voiding contractions was evaluated according to the method of Dray (J. Pharmacol. Methods, 13:157, 1985), with some modifications as in Guarneri (Pharmacol. Res., 27:173, 1993). Briefly, rats were anesthetized by subcutaneous injection of 1.25 g/kg (5 ml/kg) urethane, after which the urinary bladder was catheterized via the urethra using PE 50 polyethylene tubing filled with physiological saline. The catheter was tied in place with a ligature around the external urethral orifice and was connected with conventional pressure transducers (Statham P23 ID/P23 XL). The intravesical pressure was displayed continuously on a chart recorder (Battaglia Rangoni KV 135 with DCI/TI amplifier). The bladder was then filled via the recording catheter by incremental volumes of warm (37° C.) saline until reflex bladder voiding contractions occurred (usually 0.8–1.5 ml). For intravenous (i.v.) injection of bioactive compounds, PE 50 polyethylene tubing filled with physiological saline was inserted into the jugular vein.

From the cystometrogram, the number of contractions recorded 15 min before (basal values) and after treatment, as well as the mean amplitude of these contractions (mean height of the peaks in mmHg) was evaluated.

Since most compounds produced an effect that was relatively rapid in onset and led to a complete cessation of bladder contractions, bioactivity was conveniently estimated by measuring the duration of bladder quiescence (i.e., the duration of time during which no contractions occurred). The number of animals tested showing a reduction in the number of contractions >30% of that observed in the basal period was also recorded.

To compare the potency of the tested compounds for inhibiting bladder voiding contractions, equieffective doses which resulted in a contraction disappearance time of 10 minutes ($ED_{10min}$) were computed by means of least square linear regression analysis. Also computed in this manner were extrapolated doses which induced a reduction of the number of contractions of greater than 30% in 50% of treated rats ($ED_{50}$, frequency) by the method of Bliss (Bliss C. I., Quart J. Pharm. Pharmacol. 11, 192–216, 1938). After the suppressive effects of drug injection wore off, the height of the contractile peaks was compared with the height of the peaks previously recorded after the control intravenous administration of vehicle. The potency of the tested compounds ($ED_{50}$ value: the extrapolated doses including a 30% reduction of amplitude of the contractions in 50% of treated rats) was evaluated on a quantal basis by the method of Bliss (Bliss C. I., Quart. J. Pharm. Pharmacol. 11, 192–216, 1938).

B. Results

The rapid distension of the urinary bladder in urethane-anesthetized rats produced a series of rhythmic bladder voiding contractions whose characteristics have been described and are well-known in the art (Maggi et al., Brain Res., 380:83, 1986; Maggi, et al., J. Pharmacol. Exp. Ther., 230:500, 1984). The frequency of these contractions is related to the sensory afferent arm of reflex micturition and to the integrity of the micturition center, while their amplitude is a property of the efferent arm of the reflex. In this model system, compounds that act mainly on the CNS (such as morphine) cause a block in voiding contraction, whereas drugs that act at the level of the detrusor muscle, such as oxybutynin, lower the amplitude of the bladder contractions.

The results obtained after administration of prior art compounds and compounds of the invention are shown in Table 1.

Compound A, a prior art compound, was more potent than flavoxate and oxybutynin in inhibiting voiding contractions. This compound, in contrast to oxybutynin, did not affect the amplitude of the contraction, indicating no impairment of bladder contractility.

Surprisingly, however, compounds with substituents at position 2 of the aniline ring in Formula I, such as $NO_2$, such as the compound of Example 2, have significantly higher potency than unsubstituted compound A, particular with regard to the $ED_{10min}$ values. Like compound A, the compound of Example 2 does not affect bladder contractility. When compounds were synthesized with a nitro group at position 3 or 4 of the aniline ring, such as comparative compounds B and C, pharmacological activity was abolished.

Results similar (i.e., higher potency for the 2-substituted derivatives) to those obtained by Example 2 were obtained relative to compounds where R is H and which are unsubstituted or substituted at the 3- and 4-positions of the aniline ring. These results are shown in Table 1, where it can be seen that compounds AA, D, E, which are unsubstituted and 3- and 4-substituted compounds, are clearly inferior to the compounds of Examples 1, 10 and 11 and 18, i.e., 2-$NO_2$, 2-CN, 2-$COCH_3$ and 2-$COOCH_3$ derivatives. The compounds of the invention were clearly superior, particularly with regard to the $ED_{50}$ values which are indicators of urinary frequency.

TABLE 1

Effects on rhythmic bladder voiding contractions after intravenous administration. Data represent the $ED_{10min}$ values (the extrapolated dose inducing 10 min of disappearance of the contractions); the $ED_{50}$ values (the extrapolated doses inducing a reduction of the number of contractions >30% in 50% of treated rats) (frequency), and the $ED_{50}$ values (the extrapolated doses inducing 30% reduction of amplitude of the contractions in 50% of treated rats) (amplitude).

| Compound | $ED_{10min}$ μg/kg | ED50 (frequency) μg/kg | ED50 (amplitude) μg/kg |
|---|---|---|---|
| Compound A | 650 | 33 | n.a. |
| Compound B | >1000 | >1000 | n.a. |
| Compound C | >1000 | >1000 | n.a. |
| Compound D | >1000 | >1000 | n.a. |
| Compound E | >1000 | >1000 | n.a. |
| Compound AA | 663 | 244 | n.a. |
| Example 1 | 192 | 55 | n.a. |
| Example 2 | 60 | 9 | n.a. |
| Example 10 | 122 | 28 | n.a. |
| Example 11 | 318 | 40 | n.a. |
| Example 13 | 266 | 29 | n.a. |
| Example 18 | 101 | 17 | n.a |
| Example 20 | 97 | 25 | n.a. |
| Example 23 | 93 | 18 | n.a. |
| Example 27 | 131 | 13 | n.a. |
| Flavoxate | >10000 | 2648 | n.a. |
| Oxybutinin | 7770 | >10000 | 240 | n.a. = not active; no significant reduction of the height of peaks
Compound AA = 1-(N-phenyl-2-aminoethyl)-4-(2-methoxyphenyl)piperazine
Compounds A, B, C, D, E see text.

EXAMPLE 47

Effects on Cystometric Parameters in Conscious Rats

A. Methods:

Male Sprague Dawley rats (Crl: CDo BR) weighing 250–350 g were used. The animals were housed with free access to food and water and maintained on a forced 12 h alternating light-dark cycle at 22–24° C. for at least one week, except during performance of the experiment. To quantify urodynamic parameters in conscious rats, cystometrographic studies were performed using procedures previously described (Guarneri et al., Pharmacol. Res., 24:175, 1991). Male rats were anesthetized with nembutal (30 mg/kg) and chloral hydrate (125 mg/kg) i.p. and were placed in a supine position. An approximately 10 mm long midline incision was made in the shaved and cleaned abdominal wall. The urinary bladder was gently freed from adhering tissues, emptied, and then cannulated, via an incision at the dome, with a polyethylene cannula (Portex PP30), which was permanently sutured with silk thread. The cannula was exteriorized through a subcutaneous tunnel in the retroscapular area, where it was connected with a plastic adapter to avoid the risk of removal by the animal. For intravenous (i.v.) injection of test compounds, a PE 50 polyethylene tubing filled with physiological saline was inserted into the jugular vein and exteriorized in the retroscapular area. The rats were utilitized exclusively one day after implantation. On the day of the experiment, the rats were placed in Bollman's cages; after a stabilization period of 20 min, and the free tip of the bladder catheter was connected through a T-shaped tube to a pressure transducer (Bentley T 800/Marb P 82) and to a peristaltic pump (Gilson minipuls 2) for a continuous infusion, at the constant rate of 0.1 ml/min, of saline solution into the urinary bladder. The intraluminal pressure signal during infusion was continuously recorded on a polygraph (Battaglia Rangoni KO 380 with ADCl/T amplifier).

Two urodynamic parameters were evaluated: bladder volume capacity (BVC) and micturition pressure (MP). BVC (in ml) is defined as the minimum volume infused after which detrusor contraction (followed by micturition) occurs. MP (in mm Hg) is defined as the maximal intravesical pressure induced by the contraction of detrusor during micturition. Basal BVC and MP values were calculated as the means of the first two recorded cystometrograms. At this point in the assay, the infusion was interrupted and the test compounds were administered. Fifteen minutes after intravenous administration two additional cystometrograms were recorded in each animal and the mean values of the two cystometrographic parameters were calculated. The statistical significance of the differences in urodynamic parameter values was evaluated by Student's t test for paired data.

B. Results:

The effects of different doses of the tested compounds are shown in Table 2. Compound A behaved similarly to flavoxate by increasing BVC. Neither compound impaired bladder contractility, since no consistent changes in MP were observed. In contrast, oxybutynin markedly and dose-dependently decreased MP without effects on BVC. The compound of Example 2 was more potent than compound A and flavoxate; a significant increase in BVC was observed after the i.v. administration of 0.3 mg/kg of the compound of Example 2, compared with the requirement for administration of 1.0 mg/kg of flavoxate or compound A. The compound of Example 2 induced a slight, albeit significant, decrease in MP. This effect, however, was not dose-dependent and was markedly lower than that induced by oxybutynin.

TABLE 2

Effects on cystometrogram in conscious rats.
Data represent mean values ± S. E. of bladder volume capacity (BVC, ml) and of micturition pressure (MP; mmHg), before and 15 min after i.v. injection of the compounds.

| COMPOUND | Dose µg/kg | BVC before | after treat. | % of change |
|---|---|---|---|---|
| Compound A | 300 | 0.81 ± 0.05 | 0.87 ± 0.05 | +7.4 |
|  | 1000 | 0.78 ± 0.11 | 0.97 ± 0.11** | +24.4 |
| Example 2 | 300 | 0.71 ± 0.09 | 0.87 ± 0.10* | +22.5 |
|  | 1000 | 0.62 ± 0.09 | 0.75 ± 0.10** | +21.0 |
| Example 8 | 300 | 0.59 ± 0.04 | 0.71 ± 0.05* | +21.0 |
|  | 1000 | 0.65 ± 0.10 | 0.88 ± 0.12** | +35.0 |
| FLAVOXATE | 300 | 0.76 ± 0.11 | 0.87 ± 0.11 | +14.5 |
|  | 1000 | 0.88 ± 0.15 | 1.11 ± 0.16** | +26.1 |
| OXYBUTYNIN | 100 | 0.82 ± 0.15 | 0.89 ± 0.18 | +8.5 |
|  | 300 | 0.83 ± 0.13 | 0.83 ± 0.12 | ±0.0 |
|  | 1000 | 0.94 ± 0.19 | 1.00 ± 0.18 | ±6.4 |

| COMPOUND | Dose µg/kg | MP before | after treat. | % of change |
|---|---|---|---|---|
| Compound A | 300 | 90.6 ± 10.4 | 85.6 ± 11.3 | −5.5 |
|  | 1000 | 90.2 ± 6.5 | 84.1 ± 5.2 | −6.8 |
| Example 2 | 300 | 95.4 ± 6.4 | 80.4 ± 6.5** | −15.7 |
|  | 1000 | 109.0 ± 12.1 | 99.6 ± 11.2* | −8.6 |
| Example 8 | 300 | 16.1 ± 17.4 | 98.3 ± 17.2** | −15.0 |
|  | 1000 | 81.3 ± 9.0 | 64.8 ± 10.5* | −20.0 |
| FLAVOXATE | 300 | 89.2 ± 10.7 | 95.0 ± 10.9 | −6.5 |
|  | 1000 | 90.4 ± 10.7 | 80.1 ± 11.1 | −11.4 |
| OXYBUTYNIN | 100 | 95.2 ± 9.2 | 77.4 ± 10.3** | −18.7 |
|  | 300 | 82.3 ± 8.7 | 50.5 ± 6.3** | −38.6 |

* = P < 0.05, ** = P < 0.01 versus basal values; Student's test for paired data

EXAMPLE 48

Radioreceptor Binding to 5-$HT_{1A}$ and other different neurotransmitter binding sites.

A. Methods:

Recombinant human $5HT_{1A}$ receptors:

Genomic clone G-21 coding for the human 5-$HT_{1A}$ serotonergic receptor is stably transfected in a human cell line (HeLa). HeLa cells were grown as monolayers in Dulbecco's modified Eagle's medium (DMEM), supplemented with 10% fetal calf serum and gentamicin (100 mg/ml), 5% $CO_2$ at 37° C. Cells were detached from the growth flask at 95% confluence by a cell scraper and were lysed in ice-cold 5 mM Tris and 5 mM EDTA buffer (pH 7.4). Homogenates were centrifuged at 40000×g×20 min and pellets were resuspended in a small volume of ice-cold 5 mM Tris and 5 mM EDTA buffer (pH 7.4) and immediately frozen and stored at −70° C. until use. On the day of experiment, cell membranes were resuspended in binding buffer: 50 mM Tris HCl (pH 7.4), 2.5 mM $MgCl_2$, 10 µM pargiline (Fargin et al., Nature 335, 358–360, 1988). Membranes were incubated in a final volume of 1 ml for 30 min at 30° C. with 0.2–1 nM [$^3$H]8-OH-DPAT, in absence or presence of competing drugs; non-specific binding was determined in the presence of 10 µM 5-HT. The incubation was stopped by addition of ice-cold Tris-HCl buffer and rapid filtration through 0.2% polyethyleneimine pretreated Whatman GF/B or Schleicher & Schuell GF52 filters.

Native 5-$HT_{2A}$ serotoninergic receptors and $α_2$-adrenoceptors (from animal tissues)

Binding studies on native $α_2$ adrenergic receptors (Diop L. et al, J. Neurochem. 41, 710–715, 1983), and 5-$HT_{2A}$ serotonergic receptors (Craig A. and Kenneth J., Life Sci. 38, 117–127, 1986) were carried out in membranes of rat cerebral cortex. Male Sprague Dawley rats (200–300 g, S D Harland/Nossan, Italy) were killed by cervical dislocation and cerebral cortexes were excised and immediately frozen in liquid nitrogen and stored at −70° C. until use. Tissues were homogenized (2×20 sec) in 50 volumes of cold 50 mM Tris-HCl buffer pH 7.4, using a Polytron homogenizer (speed 7). Homogenates were centrifuged at 49000×g for 10 min, resuspended in 50 volumes of the same buffer, incubated at 37° C. for 15 min and centrifuged and resuspended twice more. The final pellets were suspended in 100 volumes of 50 mM Tris-HCl buffer pH 7.4, containing 10 µM pargiline and 0.1% ascorbic acid ($α_2$ adrenergic receptors) or in 100 volumes of 50 mM Tris-HCl buffer pH 7.7 (5-$HT_{2A}$ serotonergic receptors). Membranes were incubated in a final volume of 1 ml for 30 min at 25° C. with 0.5–1.5 nM [$^3$H]rauwolscine ($α_2$-adrenergic receptors) or for 20 min at 37° C. with 0.7–1.3 nM [$^3$H]ketanserin (5-$HT_{2A}$ receptors), in absence or presence of competing drugs. Non-specific binding was determined in the presence of 10 μM phentolamine ($\alpha_2$-adrenergic receptors) or 2 μM ketanserin (5-HT$_{2A}$ serotoninergic receptors). The incubation was stopped by addition of ice-cold 50 mM Tris-HCl buffer and rapid filtration through 0.2% polyethyleneimine pretreated Whatman GF/B or Schleicher & Schuell GF52 filters. The filters are then washed with ice-cold buffer and the radioactivity retained on the filters was counted by liquid scintillation spectrometry.

B. Results:

The inhibition of specific binding of the radioligands by the tested drugs was analyzed to estimate the IC$_{50}$ value by using the non-linear curve-fitting program Allfit (De Lean et al., Am. J. Physiol. 235, E97–E102, 1978). The IC$_{50}$ value was converted to an affinity constant (Ki) by the equation of Cheng & Prusoff (Cheng, Y. C.; Prusoff, W. H. Biochem. Pharmacol. 22, 3099–3108, 1973).

The results shown in Table 3A demonstrate that compound A and the compound of Example 2 both have a very high affinity for 5-HT$_{1A}$ receptors, but their binding profile is different. The compound of Example 2 was much more selective than compound A for the 5-HT$_{1A}$ receptor versus the 5-HT$_{2A}$ and the $\alpha_2$-adrenoceptors. All the other compounds of the invention tested (Table 3B) had high affinity for the 5-HT$_{1A}$ receptor.

TABLE 3A

Binding affinity for the 5-HT$_{1A}$ receptor and other neurotransmitter binding sites
Data are expressed as Ki (nM).

| Compound | 5-HT$_{1A}$ | 5-HT$_{2A}$ | $\alpha_2$ |
|---|---|---|---|
| Compound A | 0.10 | 629 | 2625 |
| Example 2 | 0.05 | >10000 | >10000 |
| Example 8 | 0.36 | 1065 | 2342 |
| Example 18 | 0.60 | 1829 | 314 |

TABLE 3B

Binding affinity for the 5-HT$_{1A}$ receptor
Data are expressed as Ki (nM).

| Compound | 5-HT$_{1A}$ |
|---|---|
| Ex. 3 | 10.28 |
| Ex. 4 | 0.64 |
| Ex. 5 | 14.85 |
| Ex. 6 | 0.45 |
| Ex. 7 | 3.82 |
| Ex. 8 | 0.36 |
| Ex. 10 | 17.23 |
| Ex. 11 | 2.92 |
| Ex. 12 | 4.77 |
| Ex. 13 | 0.50 |
| Ex. 14 | 10.32 |
| Ex. 15 | 6.20 |
| Ex. 16 | 2.90 |
| Ex. 17 | 20.15 |
| Ex. 18 | 0.60 |
| Ex. 20 | 24.62 |
| Ex. 21 | 2.72 |
| Ex. 22 | 18.18 |
| Ex. 23 | 0.14 |
| Ex. 25 | 8.91 |
| Ex. 26 | 2.69 |
| Ex. 27 | 0.57 |
| Ex. 28 | 18.78 |
| Ex. 30 | 7.96 |
| Ex. 32 | 19.36 |
| Ex. 34 | 16.27 |
| Ex. 35 | 8.00 |
| Ex. 38 | 1.02 |

Measurement of Pre- and Post-Synaptic 5-HT$_{1A}$ Receptor Antagonist Activity

A. Methods:

Antagonism of hypothermia induced by 8-OH-DPAT in mice (pre-synaptic antagonism).

The antagonistic effect of the 5-HT$_{1A}$ receptor antagonists of the invention on hypothermia induced by 8-OH-DPAT was evaluated by the method of Moser (Moser, Eur.J.Pharmacol., 193:165, 1991) with minor modifications as described below. Male CD-1 mice (28–38 g) obtained from Charles River (Italy) were housed in a climate-controlled room (temperature 22±2 C.; humidity 55±15%) and maintained on a 12 h light/dark cycle with free access to food and water. On the day of experiment, mice were placed singly in clear plastic boxes under the same ambient conditions. Body temperature was measured by the insertion of a temperature probe (Termist TM-S, LSI) into the rectum to a depth of 2 cm. Rectal temperature was measured immediately prior to intravenous injection of the test compound. All animals then received 8-OH-DPAT (0.5 mg/kg s.c.) and their temperature was measured 30 min later. For each animal, temperature changes were calculated with respect to pretreatment values and the mean values were calculated for each treatment group. A linear regression equation was used in order to evaluate ID$_{50}$ values, defined as the dose of antagonist needed to block 50% of the hypothermic effect induced by 0.5 mg/kg 8-OH-DPAT administered subcutaneously.

Inhibition of forepaw treading induced by 8-OH-DPAT in rats (post-synaptic antagonism).

The inhibitory effect of 5-HT$_{1A}$ receptor antagonists on the forepaw treading induced in rats by subcutaneous injection of 8-OH-DPAT was evaluated by the method of Tricklebank (Tricklebank et al., Eur. J.Pharmacol., 117:15, 1985) with minor modifications as described below.

Male Sprague-Dawley rats (150–175 g) obtained from Charles River (Italy), were housed in a climate-controlled room and maintained on a 12 h light/dark cycle with free access to food and water. On the day of experiment, rats were placed singly in clear plastic boxes. Rats were treated with reserpine, 1 mg/kg s.c., 18–24 h before the test to deplete intracellular stores of noradrenaline. For evaluation of antagonistic activity, compounds were i.v. administered 16 min before 8-OH-DPAT (1 mg/kg s.c.). Observation sessions of 30 s duration began 3 min after treatment with the agonist and were repeated every 3 min over a period of 15 min. The appearance of the forepaw treading symptom induced by postsynaptic stimulation of the 5HT$_{1A}$ receptors was noted, and its intensity was scored using a ranked intensity scale in which: 0=absent, 1=equivocal, 2=present and 3=intense. Behavioral scores for each treated rat were accumulated over the time course (5 observation periods) and expressed as mean values of 8–10 rats. A linear regression equation was used in order to evaluate ID$_{50}$ values, defined as the dose of antagonist needed to block 50% of the forepaw treading intensity induced by 1 mg/kg 8-OH-DPAT administered subcutaneously.

B. Results:

The results are shown in Table 4. These results demonstrate that compound of Example 2 exhibits significant pre-synaptic and post-synaptic 5-HT$_{1A}$ receptor antagonist activity. Compound A, by contrast, proved at least 10 fold less active than compound of Example 2 in both models.

TABLE 4

Antagonistic activity for the pre- and post-synaptic 5-HT$_{1A}$ receptor.
Data are expressed as ID$_{50}$ in mg/kg.

| Compound | Pre-synaptic 5-HT$_{1A}$ ID$_{50}$ | Post-synaptic 5-HT$_{1A}$ ID$_{50}$ |
|---|---|---|
| Compound A | 221 | 350 |
| Example 2 | 20 | 36 |
| Example 13 | — | 82 |
| Example 18 | n.a. | 84 |
| Example 23 | — | 177 |

What is claimed is:

1. A compound of formula I:

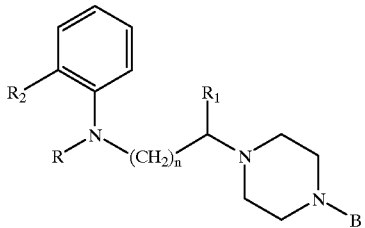

wherein
R is a cycloalkylcarbonyl, a substituted cycloalkylcarbonyl or a monocyclic heteroarylcarbonyl group,
R$_1$ is a hydrogen atom or a lower alkyl group,
R$_2$ is an alkoxy, phenoxy, nitro, cyano, acyl, amino, acylamino, alkylsulphonylamino, alkoxycarbonyl, aminocarbonyl, N-alkylaminocarbonyl, N,N-dialkylaminocarbonyl, N-acylaminocarbonyl, halo, trifluoromethyl or polyfluoroalkoxy group, n=1 or 2

B is a substituted monocyclic aryl group, an optionally substituted bicyclic aryl group, an optionally substituted bicyclic heteroaryl having 9 members with one heteroatom, or a substituted benzyl group,
with the provisos that:
if B is aryl and is substituted by an alkoxy group, then the alkoxy group must be at position 2; and
enantiomers, N-oxides, hydrates and pharmaceutically acceptable salts thereof.

2. A compound of claim 1, wherein B is 2-methoxyphenyl, R$_2$ is selected from the group consisting of nitro, trifluoromethyl, polyfluoroalkoxy, phenoxy, halogen, cyano, acyl, amino, acylamino, aminocarbonyl, alkoxycarbonyl, N-alkylaminocarbonyl, N,N-dialkylaminocarbonyl, and N-acylaminocarbonyl.

3. A compound of claim 2, wherein R is cyclohexanecarbonyl.

4. A compound of claim 1 selected from the group consisting of:
1-[N-(2-nitrophenyl)-N-cyclohexylcarbonyl-2-aminoethyl]-4-(2-methoxyphenyl)piperazine;

[1-[N-(2-trifluoromethoxyphenyl)-2-aminoethyl]-4-(2-methoxyphenyl)piperazine;]
1-[N-(2-trifluoromethoxyphenyl)-N-cyclohexylcarbonyl-2-aminoethyl]-4-(2-methoxyphenyl) piperazine;
[1-[N-(2-phenoxyphenyl)-2-aminoethyl]-4-(2-methoxyphenyl) piperazine;]
1-[N-(2-phenoxyphenyl)-N-cyclohexylcarbonyl-2-aminoethyl]-4-(2-methoxyphenyl)piperazine;
[1-[N-(2-iodophenyl)-2-aminoethyl]-4-(2-methoxyphenyl) piperazine;]
1-[N-(2-iodophenyl)-N-cyclohexylcarbonyl-2-aminoethyl]-4-(2-methoxyphenyl)piperazine;
[1-[N-(2-aminocarbonylphenyl)-2-aminoethyl]-4-(2-methoxyphenyl) piperazine;]
1-[N-(2-nitrophenyl)-N-cyclohexanecarbonyl-2-aminoethyl]-4-(4-indolyl)piperazine;
[1-[N-(2-nitrophenyl)-2-aminoethyl]-4-(2,5-dichlorobenzyl) piperazine;]
1-[N-(2-nitrophenyl)-N-cyclohexylcarbonyl-2-aminoethyl]-4-(2,5-dichlorobenzyl)piperazine;
1-[N-(2-cyclohexylcarbonylaminocarbonylphenyl)-N-cyclohexylcarbonyl-2-aminoethyl]-4-(2-methoxyphenyl)piperazine;
[1-[N-(2-methoxycarbonylphenyl)-2-aminoethyl]-4-(2-methoxyphenyl)piperazine;]
1-[N-(2-methoxycarbonylphenyl)-N-cyclohexylcarbonyl-2-aminoethyl]-4-(2-methoxyphenyl) piperazine;
[1-[N-(2-dimethylaminocarbonylphenyl)-2-aminoethyl]-4-(2-methoxyphenyl)piperazine;
1-[N-(2-methoxyphenyl)-2-aminoethyl]-4-(2-methoxyphenyl) piperazine;]
1-[N-(2-dimethylaminocarbonylphenyl)-N-cyclohexylcarbonyl-2-aminoethyl]-4-(2-methoxy phenyl)piperazine;
[1-[N-(2-trifluoromethylphenyl)-2-aminoethyl]-4-(2-methoxyphenyl)piperazine;]
1-[N-(2-methoxyphenyl)-N-cyclohexylcarbonyl-2-aminoethyl]-4-(2-methoxyphenyl)piperazine;
1-[N-(2-ethylaminocarbonylphenyl)-N-cyclohexylcarbonyl-2-aminoethyl]-4-(2-methoxyphenyl) piperazine;
1-[N-(2-trifluoromethylphenyl)-N-cyclohexylcarbonyl-2-aminoethyl]-4-(2-methoxyphenyl) piperazine;1-[N-(2-aminophenyl)-N-cyclohexylcarbonyl-2-aminoethyl]-4-(2 -methoxyphenyl)piperazine;1-[N-(2-acetylaminophenyl)-N-cyclohexylcarbonyl-2-aminoethyl]-4-(2-methoxyphenyl) piperazine;
1-[N-(2-nitrophenyl)-N-cyclohexylcarbonyl-2-aminoethyl]-4-(2-methoxyphenyl) piperazine N$^1$-oxide;1-[N-(2-nitrophenyl)-N-cyclohexylcarbonyl-2-aminoethyl]-4-(2-methoxyphenyl) piperazine N$^4$-oxide;
1-[N-(2-nitrophenyl)-N-cyclohexylcarbonyl-2-aminoethyl]-4-(2-methoxyphenyl) piperazine N$^1$,N$^4$-dioxide;
1-[N-(2-nitrophenyl)-N-(3-furylcarbonyl)-2-aminoethyl]-4-(2-methoxyphenyl) piperazine;
1-[N-(2-nitrophenyl)-N-(2-furylcarbonyl)-2-aminoethyl]-4-(2-methoxyphenyl) piperazine;
1-[N-(2-nitrophenyl)-N-(2-thiophenecarbonyl)-2-aminoethyl]-4-(2-methoxy phenyl)piperazine;
1-[N-(2-nitrophenyl)-N-(3-thiophenecarbonyl)-2-aminoethyl]-4-(2-methoxy phenyl)piperazine;

1-[N-(2-nitrophenyl)-N-(4-pyridylcarbonyl)-2-aminoethyl]-4-(2-methoxyphenyl) piperazine;

1-[N-(2-nitrophenyl)-N-(3-pyridylcarbonyl)-2-aminoethyl]-4-(2-methoxyphenyl)piperazine;

1-[N-(2-nitrophenyl)-N-(2-pyrazinylcarbonyl)-2-aminoethyl]-4-(2-methoxy phenyl) piperazine;

1-[N-(2-nitrophenyl)-N-(1-methylcyclohexylcarbonyl)-2-aminoethyl]-4-(2-methoxyphenyl) piperazine;

1-[N-(2-nitrophenyl)-N-(1-phenylcyclohexylcarbonyl)-2-aminoethyl]-4-(2-methoxyphenyl) piperazine;

[1-[N-[2-(2,2,2-trifluoroethoxy)phenyl]-2-aminoethyl]-4-(2-methoxyphenyl) piperazine;]

1-[N-[2-(2,2,2-trifluoroethoxy)phenyl]-N-cyclohexylcarbonyl-2-aminoethyl]-4-(2-methoxy phenyl)piperazine;

1-[N-(2-cyanophenyl)-N-cyclohexylcarbonyl-2-aminoethyl]-4-(2-methoxy phenyl)piperazine hypochloride;

1-[N-(2-nitrophenyl)-N-cyclohexylcarbonyl-1-amino-2-propyl]-4-(2-methoxyphenyl)pipe-razine; and pharmaceutically acceptable salts thereof.

5. A pharmaceutical composition comprising a compound of claim 1 and a pharmaceutically acceptable diluent or carrier.

6. A pharmaceutical composition comprising a compound of claim 2 and a pharmaceutically acceptable diluent or carrier.

7. A method for treating neuromuscular dysfunction of the lower urinary tract in a mammal in need of such treatment, said method comprising administering to said mammal an effective amount for treating said dysfunction of a compound of the formula

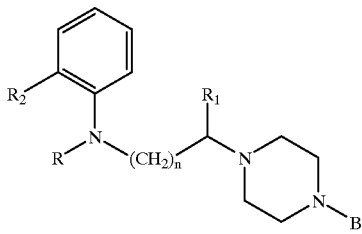

wherein
R is alkylcarbonyl cycloalkyl carbonyl, a substituted cycloalkyl carbonyl or monocyclic heteroaryl carbonyl;
$R_1$ is or a lower alkyl group;
$R_2$ is alkoxy, phenoxy, nitro, cyano, acyl amino, acylamino, alkylsulphonylamino, alkoxycarbonyl, aminocarbonyl, N-alklaminocarbonyl, N,N-dialkylamino carbonyl, N-acylamino carbonyl, halo, trifluoromethyl, or polyfluoroalkoxy group;
B is monocyclic aryl, bicyclic aryl, optionally substituted bicyclic heteroaryl having 9 members with one heteroatom or substituted benzyl;

n=1 or 2, and enantiomers, N-oxides, hydrates and pharmaceutically acceptable salts thereof.

8. The method of claim 7, wherein B is 2-methoxyphenyl, $R_2$ is selected from the group consisting of alkoxy, phenoxy, nitro, cyano, acyl, amino, acylamino, alkylsulphonylamino, alkoxycarbonyl, aminocarbonyl, N-alkylaminocarbonyl, N,N-dialkylaminocarbonyl, N-acylaminocarbonyl, halo, trifluoromethyl or polyfluoroalkoxy.

9. The method of claim 7, wherein said compound is selected from the group consisting of 1-[N-(2-nitrophenyl)-N-cyclohexylcarbonyl-2-aminoethyl]-4-(2-methoxyphenyl)piperazine;

1-[N-(2-phenoxyphenyl)-N-cyclohexylcarbonyl-2-aminoethyl]-4-(2-methoxyphenyl)piperazine;

1-[N-(2-iodophenyl)-N-cyclohexylcarbonyl-2-aminoethyl]-4-(2-methoxyphenyl)piperazine;

1-[N-(2-nitrophenyl)-N-cyclohexanecarbonyl-2-aminoethyl]-4-(4-indolyl)piperazine;

1-[N-(2-nitrophenyl)-N-cyclohexanecarbonyl-2-aminoethyl]-4-(2,5-dichlorobenzyl)piperazine;

1-[N-(2-cyclohexylcarbonylcarbamoylphenyl)-N-cyclohexylcarbonyl-2-aminoethyl]-4-(2-methoxyphenyl)piperazine;

1-[N-(2-methoxycarbonylphenyl)-N-cyclohexylcarbonyl-2-aminoethyl]-4-(2-methoxyphenyl)piperazine;

1-[N-(2-dimethylaminocarbonylphenyl)-N-cyclohexylcarbonyl-2-aminoethyl]-4-(2-methoxy phenyl)piperazine 1-[N-(2-methoxyphenyl)-N-cyclohexylcarbonyl-2-aminoethyl]-4-(2-methoxyphenyl)piperazine;

1-[N-(2-ethylaminocarbonylphenyl)-N-cyclohexylcarbonyl-2-aminoethyl]-4-(2-methoxyphenyl) piperazine;

1-[N-(2-trifluoromethylphenyl)-N-cyclohexylcarbonyl-2-aminoethyl]-4-(2-methoxyphenyl) piperazine;

1-[N-(2-aminophenyl)-N-cyclohexylcarbonyl-2-aminoethyl]-4-(2-methoxyphenyl)piperazine;

1-[N-(2-acetylaminophenyl)-N-cyclohexylcarbonyl-2-aminoethyl]-4-(2-methoxyphenyl) piperazine;

1-[N-(2-nitrophenyl)-N-cyclohexylcarbonyl-2-aminoethyl]-4-(2-methoxyphenyl) piperazine $N^1$-oxide;

1-[N-(2-nitrophenyl)-N-cyclohexylcarbonyl-2-aminoethyl]-4-(2-methoxyphenyl) piperazine $N^4$-oxide;

1-[N-(2-nitrophenyl)-N-cyclohexylcarbonyl-2-aminoethyl]-4-(2-methoxyphenyl) piperazine $N^1,N^4$-dioxide;

1-[N-(2-nitrophenyl)-N-(3-furylcarbonyl)-2-aminoethyl]-4-(2-methoxyphenyl) piperazine;

1-[N-(2-nitrophenyl)-N-(2-furylcarbonyl)-2-aminoethyl]-4-(2-methoxyphenyl) piperazine;

1-[N-(2-nitrophenyl)-N-(2-thiophenecarbonyl)-2-aminoethyl]-4-(2-methoxy phenyl)piperazine;

1-[N-(2-nitrophenyl)-N-(3-thiophenecarbonyl)-2-aminoethyl]-4-(2-methoxy phenyl)piperazine;

1-[N-(2-nitrophenyl)-N-(4-pyridylcarbonyl)-2-aminoethyl]-4-(2-methoxyphenyl) piperazine;

1-[N-(2-nitrophenyl)-N-(3-pyridylcarbonyl)-2-aminoethyl]-4-(2-methoxyphenyl) piperazine;

1-[N-(2-nitrophenyl)-N-(2-pyrazinylcarbonyl)-2-aminoethyl]-4-(2-methoxy phenyl)piperazine;

1-[N-(2-nitrophenyl)-N-(1-methylcyclohexylcarbonyl)-2-aminoethyl]-4-(2-methoxyphenyl) piperazine;

1-[N-(2-nitrophenyl)-N-(1-phenylcyclohexylcarbonyl)-2-aminoethyl]-4-(2-methoxyphenyl) piperazine;

1-[N-[2-(2,2,2-trifluoroethoxy)phenyl]-N-cyclohexylcarbonyl-2-aminoethyl]-4-(2-methoxy phenyl)piperazine;

1-[N-(2-cyanophenyl)-N-cyclohexylcarbonyl-2-aminoethyl]-4-(2-methoxy phenyl)piperazine hydrochloride;

1-[N-(2-nitrophenyl)-N-cyclohexylcarbonyl-1-amino-2-propyl]-4-(2-methoxyphenyl)piperazine; and pharmaceutically acceptable salts thereof.

10. The method of claim 7, wherein said administration is effective for ameliorating at least one of urinary urgency, increased urinary frequency, incontinence, urine leakage, enuresis, dysuria, urinary hesitancy, and difficulty in bladder emptying in said mammal.

11. A method for treating neuromuscular dysfunction of the lower urinary tract in a mammal in need of such treatment, said method comprising administering to said mammal an effective amount of a compound of claim 7 for ameliorating at least one of urinary urgency, increased urinary frequency, incontinence, urine leakage, enuresis, dysuria, urinary hesitancy, and difficult in bladder emptying in said mammal.

12. A method for treating neuromuscular dysfunction of the lower urinary tract in a mammal in need of such treatment, said method comprising administering to said mammal an effective amount of a compound of claim 9 for ameliorating at least one of urinary urgency, increased urinary frequency, incontinence, urine leakage, enuresis, dysuria, urinary hesitancy, and difficult in bladder emptying in said mammal.

13. The method of claim 7, wherein said administering is achieved using a route selected from the group consisting of oral, enteral, intravenous, intramuscular, subcutaneous, transmucosal, transdermal, and by-inhalation routes.

14. The method of claim 13, wherein said compound is administered to said mammal in an amount of between about 0.01 and 25 mg/kg/day.

15. The method of claim 14, wherein said amount is between about 0.2 and about 5 mg/kg/day.

16. The method of claim 15, wherein the amount of said compound is between about 50 and 400 mg/day.

17. The method of claim 16, wherein the amount of said compound is about 200 mg/day.

18. The method of claim 7, wherein said administering is achieved using a route selected from the group consisting of oral and transdermal routes.

19. The method of claim 18, wherein the amount of said compound is between about 0.1 and 10 mg/kg/day.

20. A pharmaceutical composition comprising a compound of claim 4 and a pharmaceutically acceptable diluent or carrier.

21. The pharmaceutical composition of claim 20 which comprises at least one excipient selected from the group consisting of lubricants, plasticizers, colorants, absorption enhancers, and bactericides.

* * * * *